(12) United States Patent
Elizondo et al.

(10) Patent No.: US 9,579,194 B2
(45) Date of Patent: Feb. 28, 2017

(54) ANCHORING STRUCTURE WITH CONCAVE LANDING ZONE

(75) Inventors: David Elizondo, Champlin, MN (US); Andrzej M. Malewicz, Minneapolis, MN (US); Matthew W. Weston, Little Canada, MN (US); Keith E. Myers, Lake Forest, CA (US)

(73) Assignee: Medtronic ATS Medical, Inc., Minneapolis, MN (US)

( * ) Notice: Subject to any disclaimer, the term of this patent is extended or adjusted under 35 U.S.C. 154(b) by 1333 days.

(21) Appl. No.: 12/603,315

(22) Filed: Oct. 21, 2009

(65) Prior Publication Data

US 2010/0100176 A1 Apr. 22, 2010

Related U.S. Application Data

(63) Continuation-in-part of application No. 11/489,663, filed on Jul. 17, 2006, now abandoned, which is a continuation-in-part of application No. 10/680,071, filed on Oct. 6, 2003, now Pat. No. 7,101,396.

(60) Provisional application No. 61/184,650, filed on Jun. 5, 2009.

(51) Int. Cl.
 *A61F 2/24* (2006.01)
(52) U.S. Cl.
 CPC .... *A61F 2/2418* (2013.01); *A61F 2220/0016* (2013.01); *A61F 2230/00* (2013.01); *A61F 2230/0013* (2013.01); *A61F 2230/0054* (2013.01); *A61F 2230/0065* (2013.01)
(58) Field of Classification Search
 CPC .................................................... A61F 2/2418

USPC ............................ 623/1.24, 1.26, 2.12–2.19
See application file for complete search history.

(56) References Cited

U.S. PATENT DOCUMENTS

| | | | |
|---|---|---|---|
| 3,540,431 A | 11/1970 | Mobin-Uddin |
| 3,587,115 A | 6/1971 | Shiley |
| 3,628,535 A | 12/1971 | Ostrowsky et al. |
| 3,642,004 A | 2/1972 | Osthagen et al. |
| 3,657,744 A | 4/1972 | Ersek |

(Continued)

FOREIGN PATENT DOCUMENTS

| | | |
|---|---|---|
| CN | 2007-100074433 | 8/2007 |
| DE | 3640745 | 6/1987 |

(Continued)

OTHER PUBLICATIONS

Andersen, H.R. et al, "Transluminal implantation of artificial heart valves. Description of a new expandable aortic valve and initial results with implantation by catheter technique in closed chest pigs." Euro. Heart J. (1992) 13:704-708.

(Continued)

*Primary Examiner* — Thomas J Sweet
*Assistant Examiner* — Cheryl Miller

(57) ABSTRACT

A method and device for reducing paravalvular leakage upon implantation of a replacement heart valve is provided. The valve assembly includes a tissue or bioprosthetic heart valve attached to an anchoring structure. The anchoring structure includes an inlet rim that is substantially C-shaped in cross section to form a concave landing zone. The anchoring structure self-seats when implanted in the sinus of a patient with the proximal and distal ends of the C-shaped inlet rim pushed against the aorta to effectively prevent paravalvular leakage.

10 Claims, 8 Drawing Sheets

(56) References Cited

U.S. PATENT DOCUMENTS

| | | |
|---|---|---|
| 3,671,979 A | 6/1972 | Moulopoulos |
| 3,714,671 A | 2/1973 | Edwards |
| 3,795,246 A | 3/1974 | Sturgeon |
| 3,839,741 A | 10/1974 | Haller |
| 3,868,956 A | 3/1975 | Alfidi et al. |
| 3,874,388 A | 4/1975 | King et al. |
| 4,035,849 A | 7/1977 | Angell et al. |
| 4,056,854 A | 11/1977 | Boretos et al. |
| 4,222,126 A | 9/1980 | Boretos et al. |
| 4,233,690 A | 11/1980 | Akins |
| 4,265,694 A | 5/1981 | Boretos |
| 4,291,420 A | 9/1981 | Reul |
| 4,297,749 A | 11/1981 | Davis et al. |
| 4,339,831 A | 7/1982 | Johnson |
| 4,343,048 A | 8/1982 | Ross et al. |
| 4,345,340 A | 8/1982 | Rosen |
| 4,470,157 A | 9/1984 | Love |
| 4,574,803 A | 3/1986 | Storz |
| 4,580,568 A | 4/1986 | Gianturco |
| 4,592,340 A | 6/1986 | Boyles |
| 4,610,688 A | 9/1986 | Silvestrini et al. |
| 4,612,011 A | 9/1986 | Kautzky |
| 4,655,771 A | 4/1987 | Wallsten |
| 4,662,885 A | 5/1987 | DiPisa, Jr. |
| 4,665,906 A | 5/1987 | Jervis |
| 4,680,031 A | 7/1987 | Alonso |
| 4,681,908 A | 7/1987 | Broderick et al. |
| 4,710,192 A | 12/1987 | Liotta et al. |
| 4,787,899 A | 11/1988 | Lazarus |
| 4,787,901 A | 11/1988 | Baykut |
| 4,796,629 A | 1/1989 | Grayzel |
| 4,819,751 A | 4/1989 | Shimada et al. |
| 4,834,755 A | 5/1989 | Silvestrini et al. |
| 4,856,516 A | 8/1989 | Hillstead |
| 4,872,874 A | 10/1989 | Taheri |
| 4,878,495 A | 11/1989 | Grayzel |
| 4,878,906 A | 11/1989 | Lindemann et al. |
| 4,883,458 A | 11/1989 | Shiber |
| 4,909,252 A | 3/1990 | Goldberger |
| 4,917,102 A | 4/1990 | Miller et al. |
| 4,922,905 A | 5/1990 | Strecker |
| 4,954,126 A | 9/1990 | Wallsten |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,007,896 A | 4/1991 | Shiber |
| 5,026,366 A | 6/1991 | Leckrone |
| 5,032,128 A | 7/1991 | Alonso |
| 5,047,041 A | 9/1991 | Samuels |
| 5,059,177 A | 10/1991 | Towne et al. |
| 5,085,635 A | 2/1992 | Cragg |
| 5,089,015 A | 2/1992 | Ross |
| 5,152,771 A | 10/1992 | Sabbaghian et al. |
| 5,163,953 A | 11/1992 | Vince |
| 5,167,628 A | 12/1992 | Boyles |
| 5,232,445 A | 8/1993 | Bonzel |
| 5,272,909 A | 12/1993 | Nguyen et al. |
| 5,295,958 A | 3/1994 | Shturman |
| 5,327,774 A | 7/1994 | Nguyen et al. |
| 5,332,402 A | 7/1994 | Teitelbaum et al. |
| 5,350,398 A | 9/1994 | Pavcnik et al. |
| 5,370,685 A | 12/1994 | Stevens |
| 5,397,351 A | 3/1995 | Pavcnik et al. |
| 5,411,552 A | 5/1995 | Andersen et al. |
| 5,415,633 A | 5/1995 | Lazarus et al. |
| 5,431,676 A | 7/1995 | Dubrul et al. |
| 5,443,446 A | 8/1995 | Shturman |
| 5,480,424 A | 1/1996 | Cox |
| 5,489,294 A | 2/1996 | McVenes et al. |
| 5,489,297 A | 2/1996 | Duran |
| 5,496,346 A | 3/1996 | Horzewski et al. |
| 5,500,014 A | 3/1996 | Quijano et al. |
| 5,545,211 A | 8/1996 | An et al. |
| 5,545,214 A | 8/1996 | Stevens |
| 5,554,185 A | 9/1996 | Block et al. |
| 5,575,818 A | 11/1996 | Pinchuk |
| 5,580,922 A | 12/1996 | Park et al. |
| 5,591,195 A | 1/1997 | Taheri et al. |
| 5,609,626 A | 3/1997 | Quijano et al. |
| 5,645,559 A | 7/1997 | Hachtman et al. |
| 5,665,115 A | 9/1997 | Cragg |
| 5,667,523 A | 9/1997 | Bynon et al. |
| 5,674,277 A | 10/1997 | Freitag |
| 5,702,368 A | 12/1997 | Stevens et al. |
| 5,713,953 A | 2/1998 | Vallana et al. |
| 5,716,417 A | 2/1998 | Girard et al. |
| 5,746,709 A | 5/1998 | Rom et al. |
| 5,749,890 A | 5/1998 | Shaknovich |
| 5,766,151 A | 6/1998 | Valley et al. |
| 5,782,809 A | 7/1998 | Umeno et al. |
| 5,800,456 A | 9/1998 | Maeda et al. |
| 5,800,508 A | 9/1998 | Goicoechea et al. |
| 5,824,041 A | 10/1998 | Lenker |
| 5,824,043 A | 10/1998 | Cottone, Jr. |
| 5,824,053 A | 10/1998 | Khosravi et al. |
| 5,824,056 A | 10/1998 | Rosenberg |
| 5,824,061 A | 10/1998 | Quijano et al. |
| 5,824,064 A | 10/1998 | Taheri |
| 5,840,081 A | 11/1998 | Andersen et al. |
| 5,843,158 A | 12/1998 | Lenker et al. |
| 5,851,232 A | 12/1998 | Lois |
| 5,855,597 A | 1/1999 | Jayaraman |
| 5,855,601 A | 1/1999 | Bessler et al. |
| 5,861,028 A | 1/1999 | Angell |
| 5,876,448 A | 3/1999 | Thompson et al. |
| 5,888,201 A | 3/1999 | Stinson et al. |
| 5,891,191 A | 4/1999 | Stinson |
| 5,906,619 A | 5/1999 | Olson et al. |
| 5,913,842 A | 6/1999 | Boyd et al. |
| 5,925,063 A | 7/1999 | Khosravi |
| 5,944,738 A | 8/1999 | Amplatz et al. |
| 5,957,949 A | 9/1999 | Leonhardt et al. |
| 5,968,068 A | 10/1999 | Dehdashtian et al. |
| 5,984,957 A | 11/1999 | Laptewicz, Jr. et al. |
| 5,997,573 A | 12/1999 | Quijano et al. |
| 6,022,370 A | 2/2000 | Tower |
| 6,027,525 A | 2/2000 | Suh et al. |
| 6,029,671 A | 2/2000 | Stevens et al. |
| 6,042,589 A | 3/2000 | Marianne |
| 6,042,598 A | 3/2000 | Tsugita et al. |
| 6,042,607 A | 3/2000 | Williamson, IV |
| 6,051,014 A | 4/2000 | Jang |
| 6,059,809 A | 5/2000 | Amor et al. |
| 6,110,201 A | 8/2000 | Quijano et al. |
| 6,146,366 A | 11/2000 | Schachar |
| 6,159,239 A | 12/2000 | Greenhalgh |
| 6,162,208 A | 12/2000 | Hipps |
| 6,162,245 A | 12/2000 | Jayaraman |
| 6,168,614 B1 | 1/2001 | Anderson |
| 6,171,335 B1 | 1/2001 | Wheatley et al. |
| 6,200,336 B1 | 3/2001 | Pavcnik et al. |
| 6,203,550 B1 | 3/2001 | Olson |
| 6,210,408 B1 | 4/2001 | Chandrasekaran et al. |
| 6,218,662 B1 | 4/2001 | Tchakarov et al. |
| 6,221,006 B1 | 4/2001 | Dubrul et al. |
| 6,221,091 B1 | 4/2001 | Khosravi |
| 6,241,757 B1 | 6/2001 | An et al. |
| 6,245,102 B1 | 6/2001 | Jayaraman |
| 6,248,116 B1 | 6/2001 | Chevillon et al. |
| 6,258,114 B1 | 7/2001 | Konya et al. |
| 6,258,115 B1 | 7/2001 | Dubrul |
| 6,258,120 B1 | 7/2001 | McKenzie et al. |
| 6,277,555 B1 | 8/2001 | Duran et al. |
| 6,299,637 B1 | 10/2001 | Shaolian et al. |
| 6,302,875 B1 | 10/2001 | Makower et al. |
| 6,302,906 B1 | 10/2001 | Goicoechea et al. |
| 6,309,382 B1 | 10/2001 | Garrison et al. |
| 6,309,417 B1 | 10/2001 | Spence et al. |
| 6,338,735 B1 | 1/2002 | Stevens |
| 6,348,063 B1 | 2/2002 | Yassour et al. |
| 6,350,277 B1 | 2/2002 | Kocur |
| 6,352,708 B1 | 3/2002 | Duran et al. |
| 6,371,970 B1 | 4/2002 | Khosravi et al. |

(56) References Cited

U.S. PATENT DOCUMENTS

| | | | |
|---|---|---|---|
| 6,371,983 B1 | 4/2002 | Lane |
| 6,379,383 B1 | 4/2002 | Palmaz et al. |
| 6,380,457 B1 | 4/2002 | Yurek et al. |
| 6,398,807 B1 | 6/2002 | Chouinard et al. |
| 6,409,750 B1 | 6/2002 | Hyodoh et al. |
| 6,425,916 B1 | 7/2002 | Garrison |
| 6,440,164 B1 | 8/2002 | DiMatteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,303 B1 | 10/2002 | Amplatz et al. |
| 6,475,239 B1 | 11/2002 | Campbell et al. |
| 6,482,228 B1 | 11/2002 | Norred |
| 6,488,704 B1 | 12/2002 | Connelly et al. |
| 6,494,909 B2 | 12/2002 | Greenhalgh |
| 6,503,272 B2 | 1/2003 | Duerig et al. |
| 6,508,833 B2 | 1/2003 | Pavcnik et al. |
| 6,527,800 B1 | 3/2003 | McGuckin, Jr. et al. |
| 6,530,949 B2 | 3/2003 | Konya et al. |
| 6,530,952 B2 | 3/2003 | Vesely |
| 6,558,417 B2 | 5/2003 | Peredo |
| 6,558,418 B2 | 5/2003 | Carpentier |
| 6,562,031 B2 | 5/2003 | Chandrasekaran et al. |
| 6,562,058 B2 | 5/2003 | Seguin et al. |
| 6,569,196 B1 | 5/2003 | Vesely |
| 6,582,462 B1 | 6/2003 | Andersen |
| 6,585,758 B1 | 7/2003 | Chouinard et al. |
| 6,592,546 B1 | 7/2003 | Barbut et al. |
| 6,605,112 B1 | 8/2003 | Moll et al. |
| 6,613,077 B2 | 9/2003 | Gilligan et al. |
| 6,622,604 B1 | 9/2003 | Chouinard et al. |
| 6,635,068 B1 | 10/2003 | Dubrul et al. |
| 6,652,571 B1 | 11/2003 | White et al. |
| 6,652,578 B2 | 11/2003 | Bailey et al. |
| 6,656,213 B2 | 12/2003 | Solem |
| 6,663,663 B2 | 12/2003 | Kim et al. |
| 6,669,724 B2 | 12/2003 | Park et al. |
| 6,673,089 B1 | 1/2004 | Yassour et al. |
| 6,673,109 B2 | 1/2004 | Cox |
| 6,676,698 B2 | 1/2004 | McGuckin, Jr. et al. |
| 6,682,558 B2 | 1/2004 | Tu et al. |
| 6,682,559 B2 | 1/2004 | Myers |
| 6,685,739 B2 | 2/2004 | DiMatteo et al. |
| 6,689,144 B2 | 2/2004 | Gerberding |
| 6,689,164 B1 | 2/2004 | Seguin |
| 6,692,512 B2 | 2/2004 | Jang |
| 6,692,513 B2 | 2/2004 | Streeter et al. |
| 6,695,878 B2 | 2/2004 | McGuckin, Jr. et al. |
| 6,702,851 B1 | 3/2004 | Chinn et al. |
| 6,719,789 B2 | 4/2004 | Cox |
| 6,730,118 B2 | 5/2004 | Spenser |
| 6,730,377 B2 | 5/2004 | Wang |
| 6,733,525 B2 | 5/2004 | Yang |
| 6,736,846 B2 | 5/2004 | Cox |
| 6,752,828 B2 | 6/2004 | Thornton |
| 6,758,855 B2 | 7/2004 | Fulton, III et al. |
| 6,767,362 B2 | 7/2004 | Schreck |
| 6,769,434 B2 | 8/2004 | Liddicoat et al. |
| 6,786,925 B1 | 9/2004 | Schoon |
| 6,790,229 B1 | 9/2004 | Berreklouw |
| 6,792,979 B2 | 9/2004 | Konya et al. |
| 6,797,002 B2 | 9/2004 | Spence |
| 6,821,297 B2 | 11/2004 | Snyders |
| 6,830,575 B2 | 12/2004 | Stenzel et al. |
| 6,830,584 B1 | 12/2004 | Seguin |
| 6,830,585 B1 | 12/2004 | Artof |
| 6,846,325 B2 | 1/2005 | Liddicoat |
| 6,866,650 B2 | 3/2005 | Stevens |
| 6,872,223 B2 | 3/2005 | Roberts |
| 6,875,231 B2 | 4/2005 | Anduiza et al. |
| 6,883,522 B2 | 4/2005 | Spence et al. |
| 6,887,266 B2 | 5/2005 | Williams et al. |
| 6,890,330 B2 | 5/2005 | Streeter et al. |
| 6,893,460 B2 | 5/2005 | Spenser et al. |
| 6,896,690 B1 | 5/2005 | Lambrecht et al. |
| 6,908,481 B2 | 6/2005 | Cribier |
| 6,913,600 B2 | 7/2005 | Valley et al. |
| 6,929,653 B2 | 8/2005 | Streeter |
| 6,936,066 B2 | 8/2005 | Palmaz et al. |
| 6,939,365 B1 | 9/2005 | Fogarty et al. |
| 6,951,571 B1 | 10/2005 | Srivastava |
| 6,974,474 B2 | 12/2005 | Pavcnik et al. |
| 6,974,476 B2 | 12/2005 | McGuckin et al. |
| 6,986,742 B2 | 1/2006 | Hart et al. |
| 6,989,027 B2 | 1/2006 | Allen et al. |
| 6,989,028 B2 | 1/2006 | Lashinski et al. |
| 6,991,649 B2 | 1/2006 | Sievers |
| 7,018,401 B1 | 3/2006 | Hyodoh et al. |
| 7,041,128 B2 | 5/2006 | McGuckin, Jr. et al. |
| 7,044,966 B2 | 5/2006 | Svanidze et al. |
| 7,048,014 B2 | 5/2006 | Hyodoh et al. |
| 7,097,659 B2 | 8/2006 | Woolfson et al. |
| 7,101,396 B2 | 9/2006 | Artof et al. |
| 7,105,016 B2 | 9/2006 | Shiu et al. |
| 7,115,141 B2 | 10/2006 | Menz et al. |
| 7,128,759 B2 | 10/2006 | Osborne et al. |
| 7,147,663 B1 | 12/2006 | Berg et al. |
| 7,153,324 B2 | 12/2006 | Case et al. |
| 7,160,319 B2 | 1/2007 | Chouinard et al. |
| 7,175,656 B2 | 2/2007 | Khairkhahan |
| 7,186,265 B2 | 3/2007 | Sharkawy et al. |
| 7,195,641 B2 | 3/2007 | Palmaz et al. |
| 7,198,646 B2 | 4/2007 | Figulla et al. |
| 7,201,761 B2 | 4/2007 | Woolfson et al. |
| 7,201,772 B2 | 4/2007 | Schwammenthal et al. |
| 7,252,682 B2 | 8/2007 | Seguin |
| 7,300,457 B2 | 11/2007 | Palmaz |
| 7,300,463 B2 | 11/2007 | Liddicoat |
| 7,316,706 B2 | 1/2008 | Bloom et al. |
| 7,329,278 B2 | 2/2008 | Seguin |
| 7,335,218 B2 | 2/2008 | Wilson et al. |
| 7,338,520 B2 | 3/2008 | Bailey et al. |
| 7,374,571 B2 | 5/2008 | Pease et al. |
| 7,377,938 B2 | 5/2008 | Sarac et al. |
| 7,381,218 B2 | 6/2008 | Schreck |
| 7,384,411 B1 | 6/2008 | Condado |
| 7,429,269 B2 | 9/2008 | Schwammenthal et al. |
| 7,442,204 B2 | 10/2008 | Schwammenthal et al. |
| 7,462,191 B2 | 12/2008 | Spenser et al. |
| 7,470,284 B2 | 12/2008 | Lambrecht et al. |
| 7,481,838 B2 | 1/2009 | Carpentier et al. |
| 7,530,995 B2 | 5/2009 | Quijano et al. |
| 7,544,206 B2 | 6/2009 | Cohn et al. |
| 7,547,322 B2 | 6/2009 | Sarac et al. |
| 7,556,646 B2 | 7/2009 | Yang et al. |
| 7,993,394 B2* | 8/2011 | Hariton ............... A61F 2/2412 623/2.17 |
| 8,808,366 B2* | 8/2014 | Braido ............... A61F 2/2418 623/1.26 |
| 9,364,321 B2* | 6/2016 | Alkhatib ............. A61F 2/2418 |
| 2001/0001314 A1 | 5/2001 | Davison et al. |
| 2001/0002445 A1 | 5/2001 | Vesely |
| 2001/0007956 A1 | 7/2001 | Letac et al. |
| 2001/0010017 A1 | 7/2001 | Letac |
| 2001/0011189 A1 | 8/2001 | Drasler et al. |
| 2001/0021872 A1 | 9/2001 | Bailey et al. |
| 2001/0025196 A1 | 9/2001 | Chinn et al. |
| 2001/0032013 A1 | 10/2001 | Marton |
| 2001/0039450 A1 | 11/2001 | Pavcnik et al. |
| 2001/0041928 A1 | 11/2001 | Pavcnik et al. |
| 2001/0044647 A1 | 11/2001 | Pinchuk et al. |
| 2002/0010508 A1 | 1/2002 | Chobotov |
| 2002/0029014 A1 | 3/2002 | Jayaraman |
| 2002/0032480 A1 | 3/2002 | Spence et al. |
| 2002/0032481 A1 | 3/2002 | Gabbay |
| 2002/0035396 A1 | 3/2002 | Heath |
| 2002/0042650 A1 | 4/2002 | Vardi et al. |
| 2002/0052651 A1 | 5/2002 | Myers et al. |
| 2002/0058995 A1 | 5/2002 | Stevens |
| 2002/0072789 A1 | 6/2002 | Hackett et al. |
| 2002/0099439 A1 | 7/2002 | Schwartz et al. |
| 2002/0103533 A1 | 8/2002 | Langberg et al. |
| 2002/0107565 A1 | 8/2002 | Greenhalgh |
| 2002/0111674 A1 | 8/2002 | Chouinard et al. |

(56) References Cited

U.S. PATENT DOCUMENTS

| | | |
|---|---|---|
| 2002/0123802 A1 | 9/2002 | Snyders |
| 2002/0133183 A1 | 9/2002 | Lentz et al. |
| 2002/0138138 A1 | 9/2002 | Yang |
| 2002/0151970 A1 | 10/2002 | Garrison |
| 2002/0161392 A1 | 10/2002 | Dubrul |
| 2002/0161394 A1 | 10/2002 | Macoviak et al. |
| 2002/0193871 A1 | 12/2002 | Beyersdorf et al. |
| 2003/0014104 A1 | 1/2003 | Cribier |
| 2003/0023300 A1 | 1/2003 | Bailey et al. |
| 2003/0023303 A1 | 1/2003 | Palmaz et al. |
| 2003/0028247 A1 | 2/2003 | Cali |
| 2003/0036791 A1 | 2/2003 | Philipp et al. |
| 2003/0040771 A1 | 2/2003 | Hyodoh et al. |
| 2003/0040772 A1 | 2/2003 | Hyodoh et al. |
| 2003/0040792 A1* | 2/2003 | Gabbay .................. 623/2.11 |
| 2003/0050694 A1 | 3/2003 | Yang et al. |
| 2003/0055495 A1 | 3/2003 | Pease et al. |
| 2003/0060875 A1 | 3/2003 | Wittens |
| 2003/0065386 A1 | 4/2003 | Weadock |
| 2003/0069492 A1 | 4/2003 | Abrams et al. |
| 2003/0109924 A1 | 6/2003 | Cribier |
| 2003/0125795 A1 | 7/2003 | Pavcnik et al. |
| 2003/0130726 A1 | 7/2003 | Thorpe et al. |
| 2003/0130729 A1 | 7/2003 | Paniagua et al. |
| 2003/0139804 A1 | 7/2003 | Hankh et al. |
| 2003/0149475 A1 | 8/2003 | Hyodoh et al. |
| 2003/0149476 A1 | 8/2003 | Damm et al. |
| 2003/0149478 A1 | 8/2003 | Figulla et al. |
| 2003/0153974 A1 | 8/2003 | Spenser |
| 2003/0181850 A1 | 9/2003 | Diamond et al. |
| 2003/0191519 A1 | 10/2003 | Lombardi et al. |
| 2003/0199913 A1 | 10/2003 | Dubrul et al. |
| 2003/0199963 A1 | 10/2003 | Tower et al. |
| 2003/0199971 A1 | 10/2003 | Tower et al. |
| 2003/0212410 A1 | 11/2003 | Stenzel et al. |
| 2003/0212454 A1 | 11/2003 | Scott et al. |
| 2003/0225445 A1 | 12/2003 | Derus et al. |
| 2003/0236568 A1 | 12/2003 | Hojeibane et al. |
| 2004/0019374 A1 | 1/2004 | Hojeibane et al. |
| 2004/0034411 A1 | 2/2004 | Quijano et al. |
| 2004/0039436 A1 | 2/2004 | Spenser et al. |
| 2004/0049224 A1 | 3/2004 | Buehlmann et al. |
| 2004/0049262 A1 | 3/2004 | Obermiller et al. |
| 2004/0049266 A1 | 3/2004 | Anduiza et al. |
| 2004/0082904 A1 | 4/2004 | Houde et al. |
| 2004/0088045 A1 | 5/2004 | Cox |
| 2004/0092858 A1 | 5/2004 | Wilson et al. |
| 2004/0092989 A1 | 5/2004 | Wilson et al. |
| 2004/0093005 A1 | 5/2004 | Durcan |
| 2004/0093060 A1 | 5/2004 | Sequin et al. |
| 2004/0093075 A1 | 5/2004 | Kuehne |
| 2004/0097788 A1 | 5/2004 | Mourles et al. |
| 2004/0098112 A1 | 5/2004 | DiMatteo et al. |
| 2004/0106976 A1 | 6/2004 | Bailey et al. |
| 2004/0106990 A1 | 6/2004 | Spence et al. |
| 2004/0111096 A1 | 6/2004 | Tu et al. |
| 2004/0116951 A1 | 6/2004 | Rosengart |
| 2004/0117004 A1 | 6/2004 | Osborne et al. |
| 2004/0122468 A1 | 6/2004 | Yodfat et al. |
| 2004/0122514 A1 | 6/2004 | Fogarty et al. |
| 2004/0122516 A1 | 6/2004 | Fogarty |
| 2004/0127979 A1 | 7/2004 | Wilson |
| 2004/0138742 A1 | 7/2004 | Myers et al. |
| 2004/0138743 A1 | 7/2004 | Myers et al. |
| 2004/0153146 A1 | 8/2004 | Lashinski et al. |
| 2004/0167573 A1 | 8/2004 | Williamson |
| 2004/0167620 A1 | 8/2004 | Ortiz |
| 2004/0186563 A1 | 9/2004 | Lobbi |
| 2004/0193261 A1 | 9/2004 | Berreklouw |
| 2004/0210240 A1 | 10/2004 | Saint |
| 2004/0210304 A1 | 10/2004 | Seguin et al. |
| 2004/0210307 A1 | 10/2004 | Khairkhahan |
| 2004/0215333 A1 | 10/2004 | Duran |
| 2004/0215339 A1 | 10/2004 | Drasler et al. |
| 2004/0225353 A1 | 11/2004 | McGuckin, Jr. et al. |
| 2004/0225354 A1 | 11/2004 | Allen |
| 2004/0254636 A1 | 12/2004 | Flagle et al. |
| 2004/0260389 A1 | 12/2004 | Case et al. |
| 2004/0260394 A1 | 12/2004 | Douk et al. |
| 2004/0267357 A1 | 12/2004 | Allen et al. |
| 2005/0010246 A1 | 1/2005 | Streeter |
| 2005/0010285 A1 | 1/2005 | Lambrecht et al. |
| 2005/0010287 A1 | 1/2005 | Macoviak |
| 2005/0015112 A1 | 1/2005 | Cohn et al. |
| 2005/0027348 A1 | 2/2005 | Case et al. |
| 2005/0033398 A1 | 2/2005 | Seguin |
| 2005/0043790 A1 | 2/2005 | Seguin |
| 2005/0049692 A1 | 3/2005 | Numamoto |
| 2005/0049696 A1 | 3/2005 | Siess |
| 2005/0055088 A1 | 3/2005 | Liddicoat et al. |
| 2005/0060029 A1 | 3/2005 | Le |
| 2005/0060030 A1 | 3/2005 | Lashinski et al. |
| 2005/0075584 A1* | 4/2005 | Cali .......................... 600/587 |
| 2005/0075712 A1 | 4/2005 | Biancucci |
| 2005/0075717 A1 | 4/2005 | Nguyen |
| 2005/0075719 A1 | 4/2005 | Bergheim |
| 2005/0075724 A1 | 4/2005 | Svanidze |
| 2005/0075727 A1 | 4/2005 | Wheatley |
| 2005/0075730 A1 | 4/2005 | Myers |
| 2005/0075731 A1 | 4/2005 | Artof |
| 2005/0085841 A1 | 4/2005 | Eversull et al. |
| 2005/0085842 A1 | 4/2005 | Eversull et al. |
| 2005/0085843 A1 | 4/2005 | Opolski et al. |
| 2005/0085890 A1 | 4/2005 | Rasmussen et al. |
| 2005/0085900 A1 | 4/2005 | Case et al. |
| 2005/0096568 A1 | 5/2005 | Kato |
| 2005/0096692 A1 | 5/2005 | Linder et al. |
| 2005/0096724 A1 | 5/2005 | Stenzel et al. |
| 2005/0096734 A1 | 5/2005 | Majercak et al. |
| 2005/0096735 A1 | 5/2005 | Hojeibane et al. |
| 2005/0096736 A1 | 5/2005 | Osse et al. |
| 2005/0096738 A1 | 5/2005 | Cali et al. |
| 2005/0107871 A1 | 5/2005 | Realyvasquez et al. |
| 2005/0113910 A1 | 5/2005 | Paniagua |
| 2005/0119688 A1 | 6/2005 | Bergheim |
| 2005/0131438 A1 | 6/2005 | Cohn |
| 2005/0137686 A1 | 6/2005 | Salahieh |
| 2005/0137688 A1 | 6/2005 | Salahieh et al. |
| 2005/0137689 A1* | 6/2005 | Salahieh ............... A61F 2/2418 623/2.11 |
| 2005/0137692 A1 | 6/2005 | Haug |
| 2005/0137695 A1 | 6/2005 | Salahieh |
| 2005/0137701 A1 | 6/2005 | Salahieh |
| 2005/0143807 A1 | 6/2005 | Pavcnik et al. |
| 2005/0143809 A1 | 6/2005 | Salahieh |
| 2005/0148997 A1 | 7/2005 | Valley et al. |
| 2005/0149181 A1 | 7/2005 | Eberhardt |
| 2005/0159808 A1 | 7/2005 | Johnson et al. |
| 2005/0165477 A1 | 7/2005 | Anduiza et al. |
| 2005/0187616 A1 | 8/2005 | Realyvasquez |
| 2005/0197695 A1 | 9/2005 | Stacchino et al. |
| 2005/0203549 A1 | 9/2005 | Realyvasquez |
| 2005/0203605 A1 | 9/2005 | Dolan |
| 2005/0203614 A1 | 9/2005 | Forster et al. |
| 2005/0203618 A1 | 9/2005 | Sharkawy |
| 2005/0222674 A1 | 10/2005 | Paine |
| 2005/0228495 A1 | 10/2005 | Macoviak |
| 2005/0234546 A1 | 10/2005 | Nugent |
| 2005/0240200 A1 | 10/2005 | Bergheim |
| 2005/0240262 A1 | 10/2005 | White |
| 2005/0240263 A1 | 10/2005 | Fogarty et al. |
| 2005/0261759 A1 | 11/2005 | Lambrecht et al. |
| 2005/0283962 A1 | 12/2005 | Boudjemline |
| 2006/0004439 A1 | 1/2006 | Spenser et al. |
| 2006/0004469 A1 | 1/2006 | Sokel |
| 2006/0009841 A1 | 1/2006 | McGuckin et al. |
| 2006/0052867 A1 | 3/2006 | Revuelta et al. |
| 2006/0058775 A1 | 3/2006 | Stevens et al. |
| 2006/0089711 A1 | 4/2006 | Dolan |
| 2006/0100685 A1 | 5/2006 | Seguin et al. |
| 2006/0116757 A1 | 6/2006 | Lashinski et al. |
| 2006/0135964 A1 | 6/2006 | Vesely |
| 2006/0142848 A1 | 6/2006 | Gabbay |
| 2006/0167474 A1 | 7/2006 | Bloom et al. |

(56) References Cited

U.S. PATENT DOCUMENTS

| | | |
|---|---|---|
| 2006/0178740 A1* | 8/2006 | Stacchino ............ A61F 2/2418 623/2.18 |
| 2006/0195134 A1 | 8/2006 | Crittenden |
| 2006/0195183 A1* | 8/2006 | Navia .................. A61F 2/2409 623/2.18 |
| 2006/0206192 A1 | 9/2006 | Tower et al. |
| 2006/0206202 A1 | 9/2006 | Bonhoeffer et al. |
| 2006/0212111 A1 | 9/2006 | Case et al. |
| 2006/0247763 A1 | 11/2006 | Slater |
| 2006/0259134 A1 | 11/2006 | Schwammenthal et al. |
| 2006/0259136 A1 | 11/2006 | Nguyen et al. |
| 2006/0259137 A1 | 11/2006 | Artof et al. |
| 2006/0265056 A1 | 11/2006 | Nguyen et al. |
| 2006/0271166 A1 | 11/2006 | Thill et al. |
| 2006/0271175 A1 | 11/2006 | Woolfson et al. |
| 2006/0276874 A1 | 12/2006 | Wilson et al. |
| 2006/0276882 A1 | 12/2006 | Case et al. |
| 2006/0282161 A1 | 12/2006 | Huynh et al. |
| 2007/0005129 A1 | 1/2007 | Damm et al. |
| 2007/0005131 A1 | 1/2007 | Taylor |
| 2007/0010878 A1 | 1/2007 | Rafiee et al. |
| 2007/0016286 A1 | 1/2007 | Herrmann et al. |
| 2007/0027518 A1 | 2/2007 | Case et al. |
| 2007/0027533 A1 | 2/2007 | Douk |
| 2007/0038295 A1 | 2/2007 | Case et al. |
| 2007/0043431 A1 | 2/2007 | Melsheimer |
| 2007/0043435 A1 | 2/2007 | Seguin et al. |
| 2007/0051377 A1 | 3/2007 | Douk et al. |
| 2007/0073392 A1 | 3/2007 | Heyninck-Jantz |
| 2007/0078509 A1 | 4/2007 | Lotfy et al. |
| 2007/0078510 A1 | 4/2007 | Ryan |
| 2007/0088431 A1 | 4/2007 | Bourang et al. |
| 2007/0093869 A1 | 4/2007 | Bloom et al. |
| 2007/0100439 A1 | 5/2007 | Cangialosi |
| 2007/0100440 A1 | 5/2007 | Figulla |
| 2007/0100449 A1 | 5/2007 | O'Neil et al. |
| 2007/0112415 A1 | 5/2007 | Bartlett |
| 2007/0162102 A1 | 7/2007 | Ryan et al. |
| 2007/0162113 A1 | 7/2007 | Sharkawy et al. |
| 2007/0185513 A1 | 8/2007 | Woolfson et al. |
| 2007/0203391 A1 | 8/2007 | Bloom et al. |
| 2007/0225681 A1 | 9/2007 | House |
| 2007/0232898 A1 | 10/2007 | Huynh et al. |
| 2007/0233228 A1 | 10/2007 | Eberhardt et al. |
| 2007/0233237 A1 | 10/2007 | Krivoruchko |
| 2007/0233238 A1 | 10/2007 | Huynh et al. |
| 2007/0238979 A1 | 10/2007 | Huynh et al. |
| 2007/0239254 A1 | 10/2007 | Marchand et al. |
| 2007/0239265 A1 | 10/2007 | Birdsall |
| 2007/0239266 A1 | 10/2007 | Birdsall |
| 2007/0239269 A1 | 10/2007 | Dolan et al. |
| 2007/0239273 A1 | 10/2007 | Allen |
| 2007/0244544 A1 | 10/2007 | Birdsall et al. |
| 2007/0244545 A1 | 10/2007 | Birdsall et al. |
| 2007/0244546 A1 | 10/2007 | Francis |
| 2007/0244553 A1 | 10/2007 | Rafiee et al. |
| 2007/0244554 A1 | 10/2007 | Rafiee et al. |
| 2007/0244555 A1 | 10/2007 | Rafiee et al. |
| 2007/0244556 A1 | 10/2007 | Rafiee et al. |
| 2007/0244557 A1 | 10/2007 | Rafiee et al. |
| 2007/0250160 A1 | 10/2007 | Rafiee |
| 2007/0255394 A1 | 11/2007 | Ryan |
| 2007/0255396 A1 | 11/2007 | Douk et al. |
| 2007/0270944 A1 | 11/2007 | Bergheim et al. |
| 2007/0288000 A1 | 12/2007 | Bonan |
| 2008/0004696 A1 | 1/2008 | Vesely |
| 2008/0009940 A1 | 1/2008 | Cribier |
| 2008/0015671 A1 | 1/2008 | Bonhoeffer |
| 2008/0021552 A1 | 1/2008 | Gabbay |
| 2008/0048656 A1 | 2/2008 | Tan |
| 2008/0065011 A1 | 3/2008 | Marchand et al. |
| 2008/0065206 A1 | 3/2008 | Liddicoat |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0077234 A1 | 3/2008 | Styrc |
| 2008/0082165 A1 | 4/2008 | Wilson et al. |
| 2008/0082166 A1 | 4/2008 | Styrc et al. |
| 2008/0125859 A1* | 5/2008 | Salahieh ............... A61F 2/2415 623/2.11 |
| 2008/0133003 A1 | 6/2008 | Seguin et al. |
| 2008/0140189 A1 | 6/2008 | Nguyen et al. |
| 2008/0147105 A1 | 6/2008 | Wilson et al. |
| 2008/0147180 A1 | 6/2008 | Ghione et al. |
| 2008/0147181 A1 | 6/2008 | Ghione et al. |
| 2008/0147182 A1 | 6/2008 | Righini et al. |
| 2008/0154355 A1 | 6/2008 | Benichow et al. |
| 2008/0154356 A1 | 6/2008 | Obermiller et al. |
| 2008/0161910 A1 | 7/2008 | Revuelta et al. |
| 2008/0161911 A1 | 7/2008 | Revuelta et al. |
| 2008/0183273 A1 | 7/2008 | Mesana et al. |
| 2008/0188928 A1 | 8/2008 | Salahieh et al. |
| 2008/0215143 A1 | 9/2008 | Seguin et al. |
| 2008/0215144 A1 | 9/2008 | Ryan et al. |
| 2008/0228254 A1 | 9/2008 | Ryan |
| 2008/0228263 A1 | 9/2008 | Ryan |
| 2008/0234797 A1 | 9/2008 | Styrc |
| 2008/0243246 A1 | 10/2008 | Ryan et al. |
| 2008/0255651 A1 | 10/2008 | Dwork |
| 2008/0255660 A1 | 10/2008 | Guyenot et al. |
| 2008/0255661 A1 | 10/2008 | Straubinger et al. |
| 2008/0262593 A1 | 10/2008 | Ryan et al. |
| 2008/0269878 A1 | 10/2008 | Iobbi |
| 2008/0281411 A1 | 11/2008 | Berreklouw |
| 2009/0005863 A1* | 1/2009 | Goetz et al. .................. 623/2.18 |
| 2009/0012600 A1 | 1/2009 | Styrc et al. |
| 2009/0048656 A1 | 2/2009 | Wen |
| 2009/0054976 A1 | 2/2009 | Tuval et al. |
| 2009/0069886 A1 | 3/2009 | Suri et al. |
| 2009/0069887 A1 | 3/2009 | Righini et al. |
| 2009/0069889 A1 | 3/2009 | Suri et al. |
| 2009/0085900 A1 | 4/2009 | Weiner |
| 2009/0099653 A1 | 4/2009 | Suri et al. |
| 2009/0138079 A1 | 5/2009 | Tuval et al. |
| 2009/0157175 A1* | 6/2009 | Benichou ............... A61F 2/2412 623/2.18 |
| 2009/0164004 A1 | 6/2009 | Cohn |
| 2009/0171447 A1 | 7/2009 | VonSegesser et al. |
| 2009/0192585 A1 | 7/2009 | Bloom et al. |
| 2009/0192586 A1 | 7/2009 | Tabor et al. |
| 2009/0192591 A1 | 7/2009 | Ryan et al. |
| 2009/0198316 A1 | 8/2009 | Laske et al. |
| 2009/0216310 A1 | 8/2009 | Straubinger et al. |
| 2009/0216312 A1 | 8/2009 | Straubinger et al. |
| 2009/0216313 A1 | 8/2009 | Straubinger et al. |
| 2009/0234443 A1 | 9/2009 | Ottma et al. |
| 2009/0240264 A1 | 9/2009 | Tuval et al. |
| 2009/0240320 A1 | 9/2009 | Tuval |
| 2009/0287296 A1* | 11/2009 | Manasse ............... A61F 2/2418 623/1.18 |
| 2009/0287299 A1* | 11/2009 | Tabor et al. ................. 623/1.26 |
| 2010/0036479 A1 | 2/2010 | Hill et al. |
| 2010/0049313 A1* | 2/2010 | Alon et al. ................... 623/2.11 |
| 2010/0094411 A1* | 4/2010 | Tuval .................... A61F 2/2418 623/2.1 |
| 2010/0100167 A1 | 4/2010 | Bortlein et al. |
| 2010/0131054 A1 | 5/2010 | Tuval et al. |
| 2010/0137979 A1 | 6/2010 | Tuval et al. |
| 2010/0145438 A1* | 6/2010 | Barone ................. A61F 2/2418 623/2.1 |
| 2010/0161036 A1* | 6/2010 | Pintor ................... A61F 2/2418 623/1.26 |
| 2010/0161045 A1 | 6/2010 | Righini |
| 2010/0234940 A1 | 9/2010 | Dolan |
| 2010/0268332 A1* | 10/2010 | Tuval .................... A61F 2/2418 623/2.1 |
| 2011/0022157 A1* | 1/2011 | Essinger et al. ............. 623/1.26 |
| 2011/0098802 A1* | 4/2011 | Braido et al. ................. 623/1.26 |
| 2012/0197386 A1* | 8/2012 | Von Segesser et al. ..... 623/1.24 |
| 2013/0079869 A1* | 3/2013 | Straubinger .......... A61F 2/2418 623/1.26 |

(56) References Cited

U.S. PATENT DOCUMENTS

FOREIGN PATENT DOCUMENTS

| | | |
|---|---|---|
| DE | 195 32 846 | 3/1997 |
| DE | 195 46 692 A1 | 6/1997 |
| DE | 195 46 692 C2 | 6/1997 |
| DE | 198 57 887 A1 | 7/2000 |
| DE | 199 07 646 | 8/2000 |
| DE | 100 49 812 | 4/2002 |
| DE | 100 49 813 | 4/2002 |
| DE | 100 49 815 | 4/2002 |
| EP | 1057460 A1 | 6/2000 |
| EP | 1255510 | 11/2002 |
| EP | 1469797 | 11/2005 |
| FR | 2788217 | 12/1999 |
| FR | 2815844 | 5/2000 |
| GB | 2056023 | 3/1981 |
| GB | 2433700 | 12/2007 |
| SU | 1271508 | 11/1986 |
| WO | 95/29640 | 11/1995 |
| WO | 00/47136 | 8/2000 |
| WO | 01/35870 | 5/2001 |
| WO | 01/49213 | 7/2001 |
| WO | 01/54625 | 8/2001 |
| WO | 01/62189 | 8/2001 |
| WO | 01/64137 | 9/2001 |
| WO | 02/22054 | 3/2002 |
| WO | 02/36048 | 5/2002 |
| WO | 03/003943 | 1/2003 |
| WO | 03/003949 | 1/2003 |
| WO | 03/011195 | 2/2003 |
| WO | 2004/019825 | 3/2004 |
| WO | 2004/089250 | 10/2004 |
| WO | 2005/004753 | 1/2005 |
| WO | 2005/046528 | 5/2005 |
| WO | 2006/026371 | 3/2006 |
| WO | WO2006/127756 | 11/2006 |
| WO | WO 2007-002166 | 1/2007 |
| WO | 2008/047354 | 4/2008 |
| WO | 2008/138584 | 11/2008 |
| WO | 2008/150529 | 12/2008 |
| WO | 2009/002548 | 12/2008 |
| WO | 2009/029199 | 3/2009 |
| WO | 2009/042196 | 4/2009 |
| WO | 2009/045338 | 4/2009 |
| WO | WO2009/053497 | 4/2009 |
| WO | 2009/061389 | 5/2009 |
| WO | 2009/091509 | 7/2009 |
| WO | 2009/111241 | 9/2009 |

OTHER PUBLICATIONS

Babaliaros, et al., "State of the Art Percutaneous Intervention for the Treatment of Valvular Heart Disease: A Review of the Current Technologies and Ongoing Research in the Field of Percutaneous Heart Valve Replacement and Repair," Cardiology 2007; 107:87-96.

Bailey, "Percutaneous Expandable Prosthetic Valves," In: Topol EJ, ed. Textbook of Interventional Cardiology. vol. II. Second edition. WB Saunders, Philadelphia, 1994:1268-1276.

Block, et al., "Percutaneous Approaches to Valvular Heart Disease," Current Cardiology Reports, vol. 7 (2005) pp. 108-113.

Bonhoeffer, et al, "Percutaneous Insertion of the Pulmonary Valve," Journal of the American College of Cardiology (United States), May 15, 2002, pp. 1664-1669.

Bonhoeffer, et al, "Percutaneous Replacement of Pulmonary Valve in a Right-Ventricle to Pulmonary-Artery Prosthetic Conduit with Valve Dysfunction," Lancet (England), Oct. 21, 2000, pp. 1403-1405.

Bonhoeffer, et al, "Transcatheter Implantation of a Bovine Valve in Pulmonary Position: A Lamb Study," Circulation (United States), Aug. 15, 2000, pp. 813-816.

Boudjemline, et al, "Images in Cardiovascular Medicine. Percutaneous Aortic Valve Replacement in Animals," Circulation (United States), Mar. 16, 2004, 109, p. e161.

Boudjemline, et al, "Is Percutaneous Implantation of a Bovine Venous Valve in the Inferior Vena Cava a Reliable Technique to Treat Chronic Venous Insufficiency Syndrome?" Medical Science Monitor—International Medical Journal of Experimental and Clinical Research (Poland), Mar. 2004, pp. BR61-BR66.

Boudjemline, et al, "Off-pump Replacement of the Pulmonary Valve in Large Right Ventricular Outflow Tracts: A Hybrid Approach," Journal of Thoracic and Cardiovascular Surgery (United States), Apr. 2005, pp. 831-837.

Boudjemline, et al, "Percutaneous Aortic Valve Replacement: Will We Get There?" Heart (British Cardiac Society) (England), Dec. 2001, pp. 705-706.

Boudjemline, et al, "Percutaneous Implantation of a Biological Valve in the Aorta to Treat Aortic Valve Insufficiency—A Sheep Study," Medical Science Monitor—International Medical Journal of Experimental and Clinical Research Poland), Apr. 2002, pp. BR113-BR116.

Boudjemline, et al, "Percutaneous Implantation of a Biological Valve in Aortic Position: Preliminary Results in a Sheep Study," European Heart Journal 22, Sep. 2001, p. 630.

Boudjemline, et al, "Percutaneous Implantation of a Valve in the Descending Aorta in Lambs," European Heart Journal (England), Jul. 2002, pp. 1045-1049.

Boudjemline, et al, "Percutaneous Pulmonary Valve Replacement in a Large Right Ventricular Outflow Tract: An Experimental Study," Journal of the American College of Cardiology (United States), Mar. 17, 2004, pp. 1082-1087.

Boudjemline, et al, "Percutaneous Valve Insertion: A New Approach," Journal of Thoracic and Cardiovascular Surgery (United States), Mar. 2003, pp. 741-742.

Boudjemline, et al, "Stent Implantation Combined with a Valve Replacement to Treat Degenerated Right Ventricle to Pulmonary Artery Prosthetic Conduits," European Heart Journal 22, Sep. 2001, p. 355.

Boudjemline, et al, "Steps Toward Percutaneous Aortic Valve Replacement," Circulation (United States), Feb. 12, 2002, pp. 775-778.

Boudjemline, et al, "The Percutaneous Implantable Heart Valve," Progress in Pediatric Cardiology (Ireland), 2001, pp. 89-93.

Boudjemline, et al, "Transcatheter Reconstruction of the Right Heart," Cardiology in the Young (England), Jun. 2003, pp. 308-311.

Coats, et al, "The Potential Impact of Percutaneous Pulmonary Valve Stent Implantation on Right Ventricular Outflow Tract Re-Intervention," European Journal of Cardio-Thoracic Surgery (England), Apr. 2005, pp. 536-543.

Cribier, A. et al, "Percutaneous Transcatheter Implantation of an Aortic Valve Prosthesis for Calcific Aortic Stenosis: First Human Case Description," Circulation (2002) 3006-3008.

Davidson et al., "Percutaneous therapies for valvular heart disease," Cardiovascular Pathology 15 (2006) 123-129.

Hanzel, et al., "Complications of percutaneous aortic valve replacement: experience with the Criber-Edwards™ percutaneous heart valve," EuroIntervention Supplements (2006), 1 (Supplement A) A3-A8.

Huber, et al., "Do Valved Stents Compromise Coronary Flow?" Eur. J. Cardiothorac. Surg. 2004;25:754-759.

Khambadkone, "Nonsurgical Pulmonary Valve Replacement: Why, When, and How?" Catheterization and Cardiovascular Interventions—Official Journal of the Society for Cardiac Angiography & Interventions (United States), Jul. 2004, pp. 401-408.

Khambadkone, et al, "Percutaneous Implantation of Pulmonary Valves," Expert Review of Cardiovascular Therapy (England), Nov. 2003, pp. 541-548.

Khambadkone, et al, "Percutaneous Pulmonary Valve Implantation: Early and Medium Term Results," Circulation 108 (17 Supplement), Oct. 28, 2003, p. IV-375.

Khambadkone, et al, "Percutaneous Pulmonary Valve Implantation: Impact of Morphology on Case Selection," Circulation 108 (17 Supplement), Oct. 28, 2003, p. IV-642-IV-643.

Lutter, et al, "Percutaneous Aortic Valve Replacement: An Experimental Study. I. Studies on Implantation," The Journal of Thoracic and Cardiovascular Surgery, Apr. 2002, pp. 768-776.

(56) References Cited

OTHER PUBLICATIONS

Lutter, et al, "Percutaneous Valve Replacement: Current State and Future Prospects," Annals of Thoracic Surgery (Netherlands), Dec. 2004, pp. 2199-2206.
Medtech Insight, "New Frontiers in Heart Valve Disease," vol. 7, No. 8 (2005).
Palacios, "Percutaneous Valve Replacement and Repair, Fiction or Reality?" Journal of American College of Cardiology, vol. 44, No. 8 (2004) pp. 1662-1663.
Pelton et al., "Medical Uses of Nitinol," Materials Science Forum Vols. 327-328, pp. 63-70 (2000).
Ruiz, "Transcathether Aortic Valve Implantation and Mitral Valve Repair: State of the Art," Pediatric Cardiology, vol. 26, No. 3 (2005).
Saliba, et al, "Treatment of Obstructions of Prosthetic Conduits by Percutaneous Implantation of Stents," Archives des Maldies du Coeur et des Vaisseaux (France), 1999, pp. 591-596.
Webb, et al., "Percutaneous Aortic Valve Implantation Retrograde from the Femoral Artery," Circulation (2006), 113;842-850.
Stassano et al., "Mid-term results of the valve-on-valve technique for bioprosthetic failure," Eur. J. Cardiothorac. Surg. 2000; 18:453-457.
Pavcnik et al., "Aortic and venous valve for percutaneous insertion," Min. Invas. Ther. & Allied Techol. 2000, vol. 9, pp. 287-292.

\* cited by examiner

ANCHORING STRUCTURE WITH CONCAVE LANDING ZONE

This application is a continuation in part of co-pending U.S. application Ser. No. 11/489,663 filed on Jul. 17, 2006, which is a continuation-in-part of application Ser. No. 10/680,071 filed on Oct. 6, 2003, now U.S. Pat. No. 7,101,396; and also claims priority to U.S. provisional application Ser. No. 61/184,650 filed on Jun. 5, 2009, the entireties of which are hereby incorporated by reference.

BACKGROUND OF THE INVENTION

1. Field of the Invention

The invention relates to an anchoring structure for use in minimally invasive bioprosthetic heart valve replacement systems. More particularly, the invention relates to a tubular anchoring structure with an inflow end that includes a concave landing zone that reduces paravalvular leakage.

2. Description of the Related Art

The transport of vital fluids in the human body is largely regulated by valves. Physiological valves are designed to prevent the backflow of bodily fluids, such as blood, lymph, urine, bile, etc., thereby keeping the body's fluid dynamics unidirectional for proper homeostasis. For example, venous valves maintain the upward flow of blood, particularly from the lower extremities, back toward the heart, while lymphatic valves prevent the backflow of lymph within the lymph vessels, particularly those of the limbs.

Because of their common function, valves share certain anatomical features despite variations in relative size. The cardiac valves are among the largest valves in the body with diameters that may exceed 30 mm, while valves of the smaller veins may have diameters no larger than a fraction of a millimeter. Regardless of their size, however, many physiological valves are situated in specialized anatomical structures known as sinuses. Valve sinuses can be described as dilations or bulges in the vessel wall that houses the valve. The geometry of the sinus has a function in the operation and fluid dynamics of the valve. One function is to guide fluid flow so as to create eddy currents that prevent the valve leaflets from adhering to the wall of the vessel at the peak of flow velocity, such as during systole. Another function of the sinus geometry is to generate currents that facilitate the precise closing of the leaflets at the beginning of backflow pressure. The sinus geometry is also important in reducing the stress exerted by differential fluid flow pressure on the valve leaflets or cusps as they open and close.

Thus, for example, the eddy currents occurring within the sinuses of Valsalva in the natural aortic root have been shown to be important in creating smooth, gradual and gentle closure of the aortic valve at the end of systole. Blood is permitted to travel along the curved contour of the sinus and onto the valve leaflets to effect their closure, thereby reducing the pressure that would otherwise be exerted by direct fluid flow onto the valve leaflets. The sinuses of Valsalva also contain the coronary ostia, which are outflow openings of the arteries that feed the heart muscle. When valve sinuses contain such outflow openings, they serve the additional purpose of providing blood flow to such vessels throughout the cardiac cycle.

When valves exhibit abnormal anatomy and function as a result of valve disease or injury, the unidirectional flow of the physiological fluid they are designed to regulate is disrupted, resulting in increased hydrostatic pressure. For example, venous valvular dysfunction leads to blood flowing back and pooling in the lower legs, resulting in pain, swelling and edema, changes in skin color, and skin ulcerations that can be extremely difficult to treat. Lymphatic valve insufficiency can result in lymphedema with tissue fibrosis and gross distention of the affected body part. Cardiac valvular disease may lead to pulmonary hypertension and edema, atrial fibrillation, and right heart failure in the case of mitral and tricuspid valve stenosis; or pulmonary congestion, left ventricular contractile impairment and congestive heart failure in the case of mitral regurgitation and aortic stenosis. Regardless of their etiology, all valvular diseases result in either stenosis, in which the valve does not open properly, impeding fluid flow across it and causing a rise in fluid pressure, or insufficiency/regurgitation, in which the valve does not close properly and the fluid leaks back across the valve, creating backflow. Some valves are afflicted with both stenosis and insufficiency, in which case the valve neither opens fully nor closes completely.

Because of the potential severity of the clinical consequences of valve disease, numerous surgical techniques may be used to repair a diseased or damaged heart valve. For example, these surgical techniques may include annuloplasty (contracting the valve annulus), quadrangular resection (narrowing the valve leaflets), commissurotomy (cutting the valve commissures to separate the valve leaflets), or decalcification of valve and annulus tissue. Alternatively, the diseased heart valve may be replaced by a prosthetic valve. Where replacement of a heart valve is indicated, the dysfunctional valve is typically removed and replaced with either a mechanical or tissue valve.

In the past, one common procedure has been an open-heart type procedure. However, open-heart valve repair or replacement surgery is a long and tedious procedure and involves a gross thoracotomy, usually in the form of a median sternotomy. In this procedure, a saw or other cutting instrument is used to cut the sternum longitudinally and the two opposing halves of the anterior or ventral portion of the rib cage are spread apart. A large opening into the thoracic cavity is thus created, through which the surgeon may directly visualize and operate upon the heart and other thoracic contents. Replacement heart valves typically include a sewing ring and are sutured into the annulus, resulting in a time intensive surgical procedure. The patient is typically placed on cardiopulmonary bypass for the duration of the surgery.

Minimally invasive valve replacement procedures have emerged as an alternative to open-chest surgery. A minimally invasive medical procedure is one that is carried out by entering the body through the skin or through a body cavity or anatomical opening, but with the smallest damage possible to these structures. Two types of minimally invasive valve procedures that have emerged are percutaneous valve procedures and trans-apical valve procedures. Percutaneous valve procedures pertain to making small incisions in the skin to allow direct access to peripheral vessels or body channels to insert catheters. Trans-apical valve procedures pertain to making a small incision in or near the apex of a heart to allow valve access. The distinction between percutaneous valve procedures and minimally invasive procedures is also highlighted in a recent position statement, Vassiliades Jr. T A, Block P C, Cohn L H, Adams D H, Borer J S, Feldman T, Holmes D R, Laskey W K, Lytle B W, Mack M F, Williams D O. The clinical development of percutaneous heart valve technology: a position statement of the Society of Thoracic Surgeons (STS), the American Association for Thoracic Surgery (AATS), and the Society for Cardiovascular Angiography and Interventions (SCAI). J Thorac Cardiovasc Surg 2005; 129:970-6).

As valves are implanted less and less invasively, the opportunity for suturing the valves around the annulus is reduced. However, a smaller number of sutures may increase the chance of paravalvular leakage (PVL), i.e. leakage around the valve. A smaller number of sutures may also increase the opportunities for migration and valve stability when placed in-vivo.

Tehrani discloses a superior and inferior o-ring for valve implantation in US Patent Application Publication No. 2006/0271172. Such o-rings cover the entire length of the valve and can therefore not easily be placed within the aortic sinus region. The o-rings presented by Tehrani would also block coronary outflow and adversely affect valve dynamics. The non-circular nature of the o-rings also reduces the radial force needed to adequately conform to irregularities within the implantation site, and is thus not optimal for preventing PVL and migration. The large size of the o-rings disclosed by Tehrani is also not practical as they cannot easily be collapsed down, something that is necessary for minimally invasive valve implantation.

Surgical heart valves include a sewing cuff for direct attachment to the native annulus where the surgeon relies on visual identification to correctly place the inflow ring in the annulus. Minimally invasive heart valves, however, lack any defined feature that interfaces directly with the annulus, instead relying on radial force to hold the valve in position in an attempt to prevent paravalvular leakage. Other conventional designs rely on a "feeler" to locate the native leaflets and when located deploy the valve below the feeler in an attempt to properly seat the valve in the annulus thereby preventing paravalvular leakage. Yet other conventional heart valves rely on a flange construction in which the flange uses double fabric rings to sandwich the device in the native annulus to prevent paravalvular leakage. However, the double fabric rings require additional surgical time in order for the surgeon to verify that the two rings are placed on opposite sides of the annulus.

In addition, while new less invasive valves produce beneficial results for many patients, these valves may not work as well for other patients who have calcified or irregular annuluses because a tight seal may not be formed between the replacement valve and the implantation site. Therefore, what is needed are methods, systems, and devices for reducing paravalvular leakage around heart valves while preventing valve migration and allowing valve collapsibility.

The invention is directed to solving, or at least reducing, some or all of the aforementioned problems.

SUMMARY OF THE INVENTION

The invention provides methods and systems for reducing paravalvular leakage around heart valves. As replacement valve procedures become less and less invasive, the opportunity for suturing the valves around the annulus is reduced. However, minimizing the number of sutures used to secure the replacement valve may increase the chance of paravalvular leakage (PVL), as well as the opportunities for valve migration and valve stability when placed in-vivo.

Leakage associated with a heart valve can be either paravalvular (around the valve) or central (through the valve). Examples of various heart valves include aortic valves, mitral valves, pulmonary valves, and tricuspid valves. Central leakage may be reduced by heart valve design. Paravalvular leakage, on the other hand, may be reduced by creating a seal between the replacement heart valve and the implant site to prevent blood from flowing around the replacement heart valve. It is important that the seal between the replacement heart valve and the implant site does not adversely affect the surrounding tissue. Furthermore, it is important that the seal does not affect the flow dynamics around the replacement heart valve. In the case of the aortic valve, it is also important that the seal does not obstruct coronary flow.

Accordingly, it is one object of the invention to provide methods and devices for preventing paravalvular leakage around a replacement valve, such as a heart valve, while also preventing migration. It should be noted that while reference is made herein to aortic valves, the current invention is not limited to the aortic valve. While replacement valves are typically implanted in native heart valve positions, the replacement valve systems and sealing devices discussed herein may be used to seal any type of in-vivo valve without departing from the intended scope of the invention.

In one embodiment of the invention a tubular anchoring structure with a concave landing zone is provided. The anchoring structure includes a body having a proximal or inlet end and a distal or outlet end. The inlet frame has a sinusoidal-shaped single or double rail construction and is commonly referred to as the inlet rim. The outlet frame has a sinusoidal-shaped single or double rail construction. The body of the anchoring structure may be formed of a variety of shapes such as diamond-shaped or hexagonal-shaped patterns. The sinusoidal-shaped single or double rail construction of the inlet rim is C-shaped in cross section and forms the concave landing zone of the invention.

In another embodiment of the invention, a valve assembly that reduces paravalvular leakage is provided. The valve assembly includes a bioprosthetic tissue heart valve attached to an anchoring structure. The anchoring structure includes a body having a proximal or inlet end and a distal or outlet end. The inlet frame has a sinusoidal-shaped single or double rail construction and is commonly referred to as the inlet rim. The outlet frame has a sinusoidal-shaped single or double rail construction and is commonly referred to as the outlet rim. The sinusoidal-shaped double rail construction of the inlet rim is C-shaped in cross section and forms the concave landing zone of the invention. The C-shape in cross section construction provides a bioprosthetic valve that is self-seating and that requires minimal adjustment.

In another embodiment of the invention, the C-shape in cross section construction forms a landing zone that allows the native annulus to rest in the valley of the inflow region, with the flared rails lying proximally and distally of the annulus.

In yet another embodiment of the invention, the concave landing zone of the bioprosthetic heart valve assembly provides an effective seal between the bioprosthetic replacement heart valve and the implant site to prevent paravalvular leakage.

In yet another embodiment of the invention, the inflow rim forming the concave landing zone comprises a single rail construction.

In yet another embodiment of the invention, the inflow rim forming the concave landing zone comprises a double rail construction.

In a further embodiment of the invention, the inflow rim forming the concave landing zone comprises a triple rail construction.

In a further embodiment of the invention, the construction of the single, double and/or triple rail may include a proximal portion that is longer than the distal portion to, for example, match the flaring of the aortic valve sinuses.

In another embodiment of the invention, the cross-sectional area of the inflow rim includes direct correspondence of the concave portion of the frame to the native annulus. The frame of the inflow rim engages the native annulus, with the flared inflow rails lying above and below the annulus. The radial force exerted by the self-expanding frame holds the valve in position.

The invention provides a method of preventing paravalvular leakage. Using the single, double and/or triple rail flared designs described herein, paravalvular leakage may be reduced by ensuring the inflow rim is substantially pushed against the aorta, hence forming a tight seal. In one method of implantation, a self-expanding replacement valve may be deployed into position with a delivery member, thereby pushing the inflow rim against the aorta to create a seal around the valve. In other words, a self-expandable inflow rim comprising the replacement heart valve provides the radial force necessary to position the bioprosthetic heart valve in the annulus.

It should be noted that for the purposes of this invention, the phrase "generally sinusoidal" is intended to include waves characterized by sine and cosine functions as well as waves which are not rigorously characterized by those functions, but nevertheless resemble such waves. In a more general way, such waves include those which are characterized as having one or more peaks and troughs. As an example, a wave whose peaks and troughs are U-shaped or bulbous is intended to be included. Also intended to be included, without limiting the definition, are waves which are more triangular in shape such as a saw-tooth wave or waves whose peaks and troughs are rectangular.

Although many of the above embodiments are described in reference to the aortic valve in the heart, the claimed invention may also be utilized for procedures related to other valves including, but not limited to, the mitral valve, tricuspid valve, and the pulmonary valve.

The above aspects, features and advantages of the invention will become apparent to those skilled in the art from the following description taken together with the accompanying figures.

BRIEF DESCRIPTION OF THE DRAWINGS

FIG. 1 shows an exemplary valve during normal operation.

DETAILED DESCRIPTION OF THE INVENTION

While this invention may be embodied in many different forms, there are described in detail herein various embodiments of the invention. This description is an exemplification of the principles of the invention and is not intended to limit the invention to the particular embodiments illustrated.

For the sake of consistency, the terms "peak" and "trough" are defined with respect to the proximal and distal ends of the anchoring structure in accordance with the invention. As seen in the Figures, each of the tubular anchoring structures has an inflow end, referred to herein as an inflow rim, and an outflow end, referred to herein as an outflow rim. With respect to the inflow and outflow rims "peaks" are concave relative to the proximal end of the anchoring structure and convex relative to the distal end of the anchoring structure. Troughs, on the other hand, are convex relative to the proximal end of the anchoring structure and concave relative to the distal end of the anchoring structure.

Figure 1A:
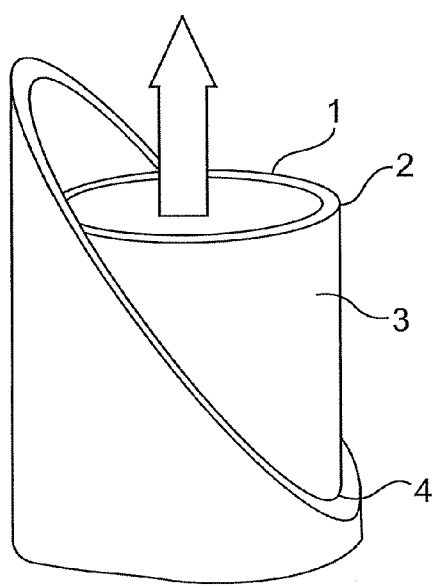
FIG. 1A shows the valve in the open position during peak flow.
Figure 1B:
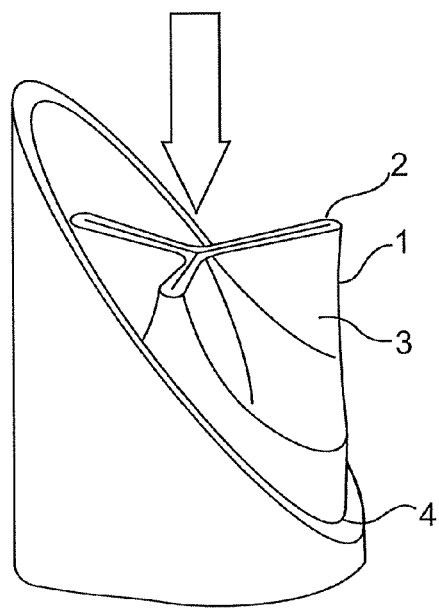
FIG. 1B shows the valve in closed position to prevent backflow of the fluid across the valve.

Turning now to the FIGS., the invention relates to methods, systems, and devices for reducing paravalvular leakage in heart valves. FIGS. 1A and 1B generally illustrate one exemplary embodiment of a heart valve 1. As illustrated in FIG. 1, valve 1 includes a distal outflow end 2, a plurality of leaflets 3, and a proximal inflow end 4. A typical valve functions similar to a collapsible tube in that it opens widely during systole or in response to muscular contraction to enable unobstructed forward flow across the valvular orifice, as illustrated in FIG. 1A. In contrast, as forward flow decelerates at the end of systole or contraction, the walls of the tube are forced centrally between the sites of attachment to the vessel wall and the valve closes completely as illustrated in FIG. 1B.

Figure 2A:
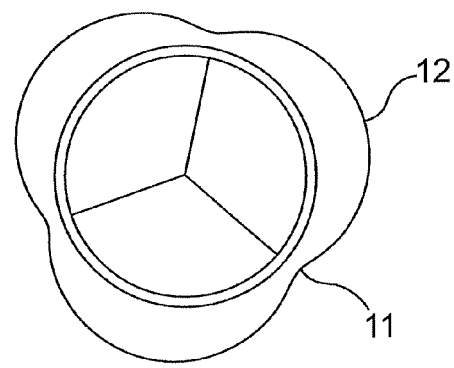
FIG. 2A is a top view illustrating the anatomy of a typical aortic valve.
Figure 2B:
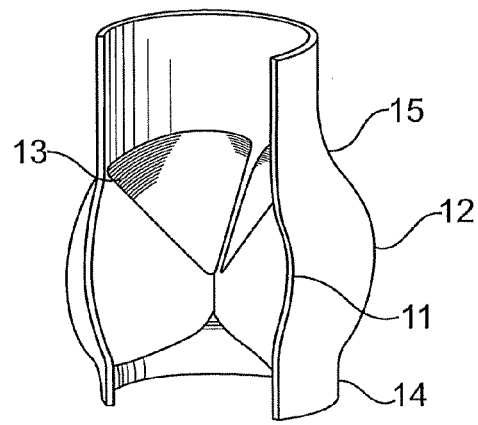
FIG. 2B is a cross-sectional view of the aortic valve of FIG. 2A.
Figure 2C:
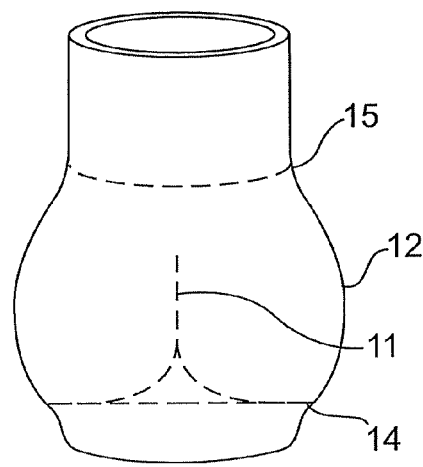
FIG. 2C is a perspective view of the aortic valve of FIG. 2A showing the inflow end, outflow end, and commissural posts in phantom lines

FIGS. 2A, 2B, and 2C illustrate the anatomy of a typical aortic valve. In particular, FIG. 2A shows a top view of a closed valve with three valve sinuses, FIG. 2B shows a perspective sectional view of the closed valve, and FIG. 2C shows a view from outside the vessel wall.

One important consideration in the design of valve replacement systems and devices is the architecture of the valve sinus. Valve sinuses 12 are dilations of the vessel wall that surround the natural valve leaflets. Typically in the aortic valve, each natural valve leaflet has a separate sinus bulge 12 or cavity that allows for maximal opening of the leaflet at peak flow without permitting contact between the leaflet and the vessel wall. As illustrated in FIGS. 2A, 2B, and 2C, the extent of the sinus 12 is generally defined by the commissures 11, vessel wall 13, inflow end 14, and outflow end 15. The proximal intersection between the sinus cavities defines the commissures 11.

FIGS. 2B and 2C also show the narrowing diameter of the sinuses at both inflow end 14 and outflow end 15, thus forming the annulus and sinotubular junction, respectively, of the sinus region. Thus, the valve sinuses form a natural compartment to support the operation of the valve by preventing contact between the leaflets and the vessel wall, which, in turn, may lead to adherence of the leaflets and/or result in detrimental wear and tear of the leaflets. The valve sinuses are also designed to share the stress conditions imposed on the valve leaflets during closure when fluid pressure on the closed leaflets is greatest. The valve sinuses further create favorable fluid dynamics through currents that soften an otherwise abrupt closure of the leaflets under conditions of high backflow pressure. Lastly, the sinuses ensure constant flow to any vessels located within the sinus cavities.

Figure 3:
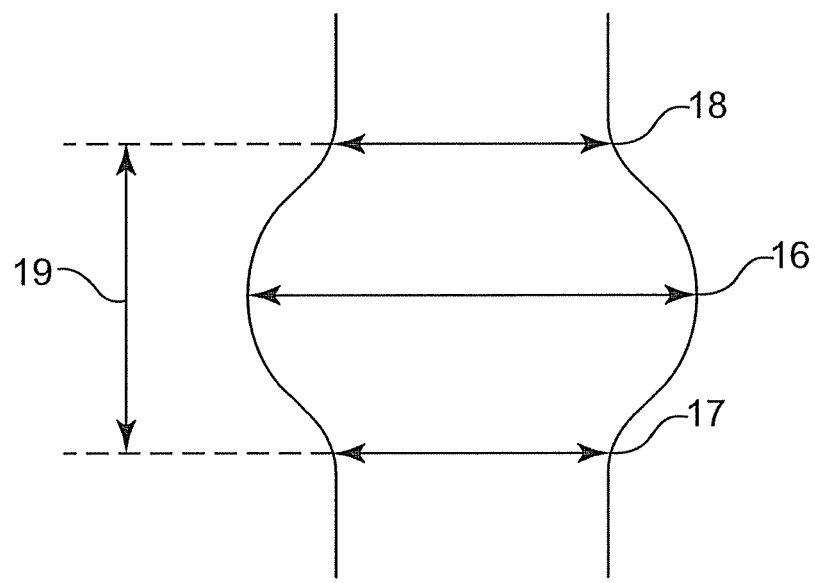
FIG. 3 is a schematic representation of the geometry and relative dimensions of the valve sinus region.

FIG. 3 is a schematic representation of the geometry and relative dimensions of the valve sinus region. As shown in FIG. 3, the valve sinus region is characterized by certain relative dimensions which remain substantially constant regardless of the actual size of the sinuses. Generally, the diameter of the sinus is at its largest at the center of the sinus cavities 16, while there is pronounced narrowing of the sinus region at both the inflow annulus 17 near the inflow end 14 and the outflow sinotubular junction 18 near the outflow end 15. Furthermore, the height of the sinus 19 (i.e. the distance between inflow annulus 17 and outflow annulus 18) remains substantially proportional to its overall dimensions. It is thus apparent that the sinus region forms an anatomical compartment with certain constant features that are uniquely adapted to house a valve. The systems and devices of the invention are designed to utilize these anatomical features of the native sinus region for optimal replacement valve function and positioning.

Figure 4:
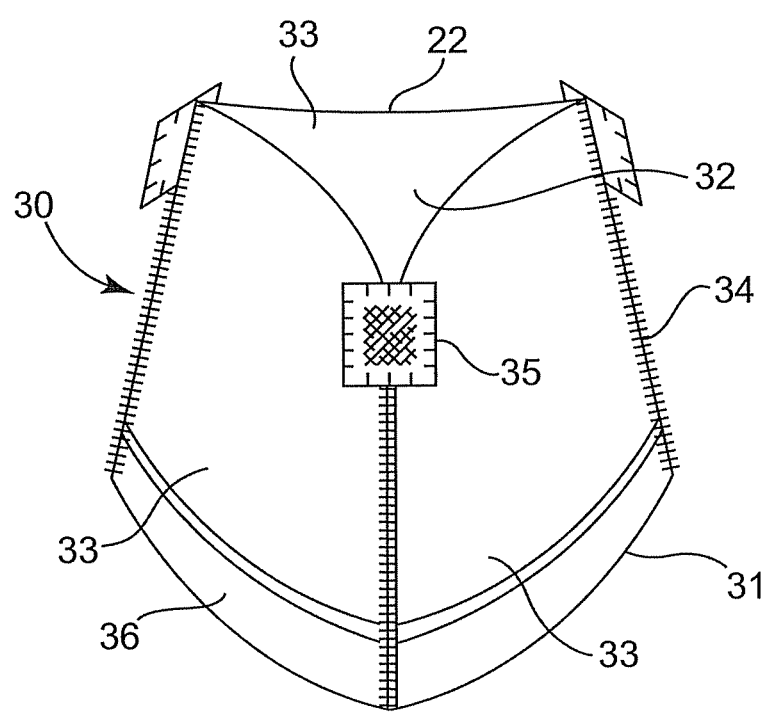
FIG. 4 is an exemplary bioprosthetic valve for use with the invention.

FIG. 4 is a perspective view of replacement valve 22, which represents one exemplary embodiment of a typical, tri-leaflet replacement valve useable with valve replacement system 20 in accordance with the invention. Replacement valve 22 includes valve body 30 having proximal inflow end 31 and a distal outflow end 32. Valve body 30 includes a plurality of valve tissue leaflets 33 joined by seams 34, wherein each seam 34 is formed by a junction of two leaflets 33. A commissural tab region 35 extends from each seam 34 at the distal end of valve body 30. Inflow end 31 of valve body 30 includes a peripheral edge that may be scalloped or straight. In addition, inflow end 31 of valve body 30 may further comprise reinforcement structure 36 that may be stitched or otherwise attached thereto.

The valve replacement systems and devices of the invention are not limited, however, to the specific valve illustrated in FIG. 4. For example, although the proximal inflow end 31 of valve body 30 is shown in FIG. 2 with a scalloped peripheral edge, other shapes and configurations are contemplated and within the intended scope of the invention. Valve leaflets 33 may be constructed of any suitable material, including but not limited to expanded polytetrafluoroethylene (ePTFE), equine pericardium, bovine pericardium, or native porcine valve leaflets similar to currently available bioprosthetic aortic valves. Other materials may prove suitable as will be appreciated by one skilled in the art.

Figure 5A:
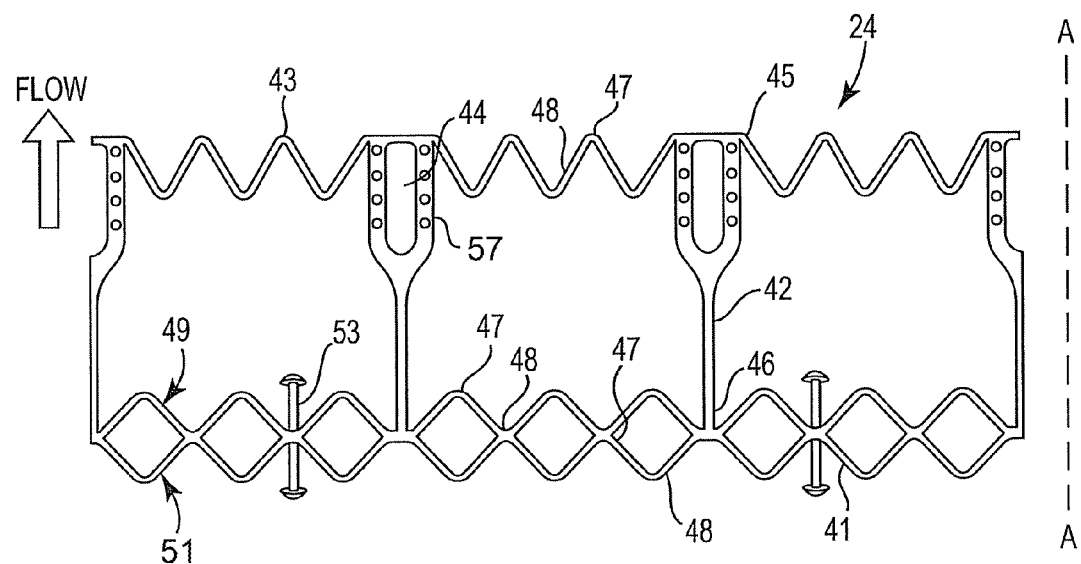
FIG. 5A is a perspective view of an exemplary embodiment of a tubular anchoring structure in accordance with the invention cut along line A-A and showing a concave landing zone.

FIG. 5A is a perspective view of an exemplary embodiment of a tubular anchoring structure in accordance with the invention cut along line A-A and laid flat and showing a concave landing zone. FIG. 5A represents one exemplary embodiment of a typical anchoring or support structure useable with valve replacement system 20 in accordance with the invention. In general, valve support structure 24 is designed as a collapsible and expandable anchoring structure adapted to support valve 22 distally along commissural tab region 35 and proximally along the proximal inflow end 31. As shown in FIG. 5A, valve 22 has been detached from valve support structure 24 so as to focus on the structure and features of the support structure.

Valve support structure 24 has a generally tubular configuration within which replacement valve 22 may be secured, and includes inflow rim 41, support posts 42 and outflow rim 43. Replacement valve 22 may be secured at the proximal inflow end 31 by attachment to inflow rim 41 of support structure 24 and at the distal outflow end 32 via commissural tabs 35 that are threaded through axially extending slots 44, which are formed in support posts 42 that extend longitudinally from inflow rim 41 to outflow rim 43 of valve support structure 24. Thus, distal ends 45 of support posts 42 contact outflow rim 43 of valve support structure 24, whereas proximal ends 46 of support posts 42 contact inflow rim 41 of valve support structure 24.

As shown in FIG. 5A outflow rim 43 of support structure 24 is depicted as comprising a single wire ring or rail that extends between support posts 42 generally at or above the axially extending slots 44 that reside therein. The outflow rim 43 is configured in an undulating or sinusoidal wave pattern forming peaks 47 and troughs 48. However, the number of rings is not important, and numerous other configurations are contemplated and may be utilized such as single, double and triple configurations of varying patterns. Inflow rim 41 is depicted as comprising a double wire ring or rail that includes a distal inflow wire ring 49 and a proximal inflow wire ring 51. Distal inflow wire ring 49 and proximal inflow wire ring 51 are configured in an undulating or sinusoidal wave pattern forming peaks 47 and troughs 48. As can be seen, the double wire rail is configured so that a peak of proximal inflow wire ring 51 connects with a trough of distal inflow wire ring 51 thus forming a diamond pattern although any number of desired shapes may be achieved such as pentagonal, hexagonal, rectangular, etc., all of which are within the scope of the invention.

The inflow rim 41 optionally includes finger-like elements 53 positioned at which distal and proximal inflow wire rings 49, 51 connect and extend in an axial direction therefrom. Finger-like elements 53 are designed to lend additional support to fabric that may cover inflow rim 41 to anchor the fabric and permit tissue ingrowth.

Figure 8:
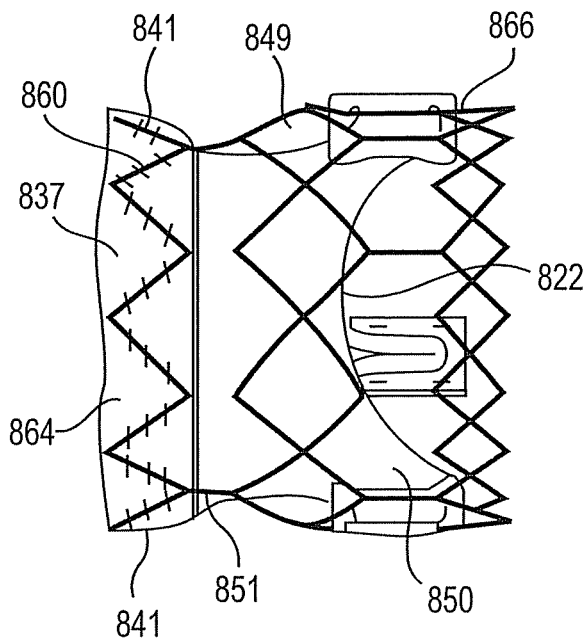
FIG. 8 depicts an exemplary embodiment of a tubular anchoring structure including a single rail flared or concave inflow rim dimensioned to lodge inside the sinus cavity.

In the embodiment of valve support structure 24 illustrated in FIG. 5A, outflow rim 43 is formed with a single ring, while inflow rim 41 is formed with a double ring that extends between support posts 42. However, the number of rings may vary, and numerous other configurations are contemplated. For example, FIG. 6A illustrates a triple ring construction for the inflow rim while FIG. 8 illustrates a single ring construction for the inflow rim.

Both inflow rim 41 and outflow rim 43 of valve support structure 24 may be formed with an undulating or sinusoidal wave-like configurations. In various embodiments of valve support structures, inflow rim 41 may have a shorter or longer wavelength (i.e., circumferential dimension from peak to peak) and/or a lesser or greater wave height (i.e., axial dimension from peak to peak) than outflow rim 43. The wavelengths and wave heights of inflow rim 41 and outflow rim 43 may be selected to ensure uniform compression and expansion of valve support structure 24 without substantial distortion. The wavelength of inflow rim 41 may be further selected to support the geometry of the inflow end of the valve attached thereto, such as the scalloped inflow end 31 of replacement valve 22 shown in FIG. 5. Notably, as shown in FIG. 5A, the undulating or sinusoidal wave pattern that forms inflow rim 41 of valve support structure 24 may be configured such that proximal ends 46 of vertical support posts 42 are connected to troughs 48 of inflow rim 41. Similarly, the undulating or sinusoidal wave-like pattern that forms outflow rim 43 of support structure 24 may be configured such that distal ends 45 of support posts 42 are connected at a peak 47 of outflow rim 43. This arrangement allows the distal inflow wire ring and proximal inflow wire ring to move together when the valve is in its radially compressed state prior to delivery thus preventing possible damage to the bioprosthetic heart valve.

Figure 6A:
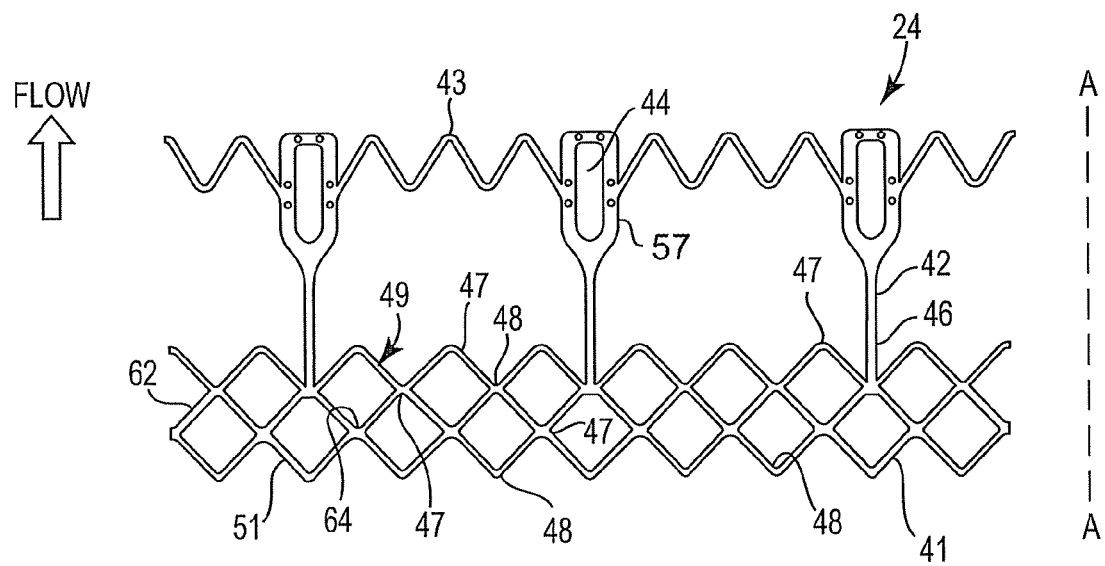
FIG. 6A is a perspective view of an exemplary embodiment of a anchoring structure in accordance with the invention cut along line A-A and showing a concave landing zone.

As shown in FIG. 6A, an alternative embodiment of an inflow rim 41 is shown. Inflow rim 41 comprises a three rail construction including a distal inflow ring 49, a proximal inflow ring 51 and a central inflow ring 62. In this alternative three-rail construction for inflow rim 41, peaks 47 of distal inflow ring 51 may be joined to the troughs 64 of central inflow ring 62. Peaks 47 of central inflow ring 62 may be joined to the troughs 48 of proximal inflow ring 49. This arrangement allows the distal inflow wire ring and proximal inflow wire ring to move together when the valve is in its radially compressed state prior to delivery thus preventing possible damage to the bioprosthetic heart valve.

FIGS. 5A and 6A further show that the distal ends 45 of support posts 42 are configured generally in the shape of a paddle with axial slot 44 extending internally within blade 57 of the paddle. Blade 57 of the paddle is oriented toward outflow rim 43 of support structure 24 and connects to outflow rim 43 at a peak of the undulating sinusoidal wave-like pattern of outflow rim 43. An important function of support posts 42 is the stabilization of valve 22 in general, and in particular the prevention of any longitudinal extension at points of valve attachment to preclude valve stretching or distortion upon compression of replacement valve system 20. Blades 57 of the paddle-shaped support posts 42 are also designed to accommodate commissural tabs 35 of valve 22.

The number of support posts 42 generally ranges from two to four, depending on the number of commissural posts present in the valve sinus. Thus, in one embodiment of the invention, valve support structure 24 comprises three support posts for a tri-leaflet replacement valve 22 with a sinus that features three natural commissural posts. Support posts 32 of valve support structure 24 may be structured to generally coincide with the natural commissural posts of the valve sinus.

Valve support structure 24 may be formed from any suitable material including, but not limited to, stainless steel or nitinol. The particular material selected for valve support structure 24 may be determined based upon whether the support structure is self-expanding or non-self-expanding. For example, preferable materials for self-expanding support structures may include shape memory materials, such as Nitinol.

Figure 5B:
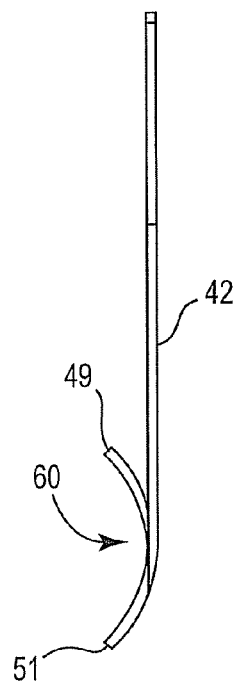
FIG. 5B is a cross-sectional view of the concave landing zone of FIG. 5A.
Figure 6B:
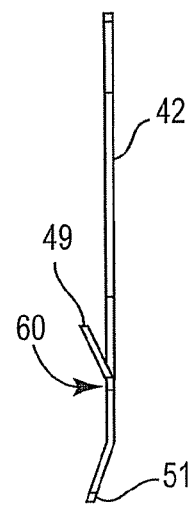
FIG. 6B is a cross-sectional view of the concave landing zone of FIG. 6A.

Turning now to FIGS. 5B and 6B a cross-sectional view of the inflow rim 41 is depicted which illustrates the concave landing zone 60 in accordance with the invention. As can be seen, peaks 47 of the distal inflow ring 49 and troughs 48 of the proximal inflow ring 51 flare outwardly so that inflow rim 41 forms a C-shape in cross section upon deployment. This cross-sectional area 61 of the inflow rim 41, or in other words the concave portion of the frame, directly corresponds to the native annulus. The frame of the inflow rim engages the native annulus, with the flared rails 47, 48 lying above and below the annulus. Upon deployment, the radial force exerted by the self-expanding frame holds the valve in position.

The concave landing zone 61 of the invention substantially prevents paravalvular leakage. Using the double, triple and single rail flared designs as best seen in FIGS. 5A, 5B, 6A, 6B, 8 and 9 paravalvular leakage may be reduced by ensuring the inflow rim 41, 841 is substantially secured proximally and distally of the annulus, hence forming a tight seal. Concave landing zone 60 allows the surgeon to easily place the bioprosthetic heart valve in the annulus thus minimizing patient time spent in surgery.

Those of ordinary skill in the art will appreciate that there are many different configurations that may be employed for the distal and proximal inflow rings 49, 51. For example, each of distal and proximal inflow rings 49, 51 may be substantially of the same vertical height. Alternatively, either of the distal or proximal inflow rings 49, 51 may be constructed to be shorter than the other depending on the anatomy of the particular patient and valve replacement involved. Those of ordinary skill in the art will appreciate, however, that both the distal inflow ring 49 and the proximal inflow ring 51 may be comprised of any number of varying vertical heights without deviating from the spirit of the invention.

Figure 7:
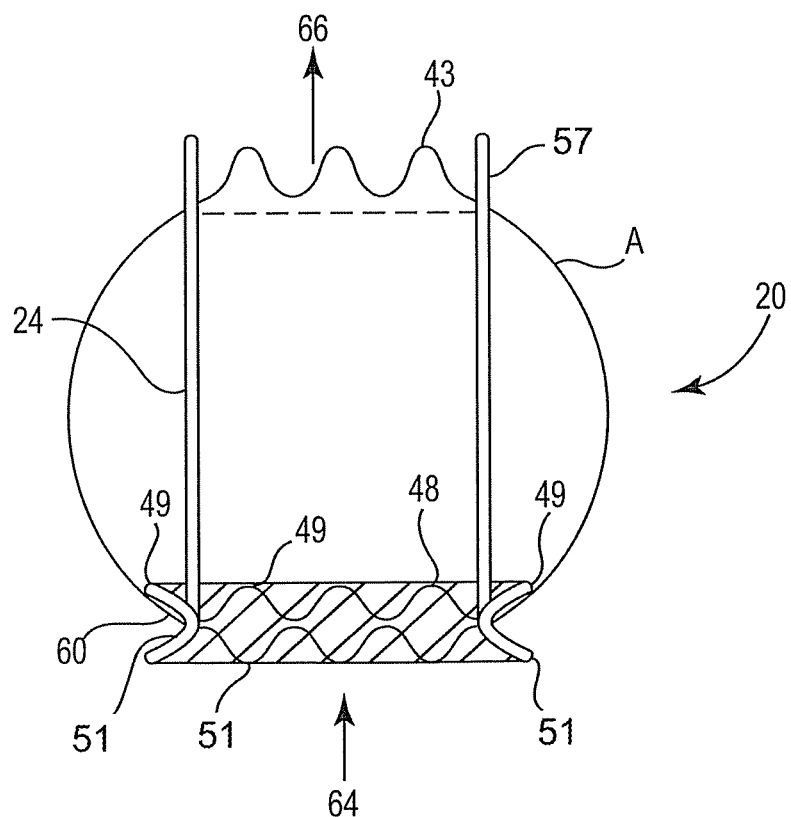
FIG. 7 depicts an exemplary embodiment of the tubular anchoring structure of FIG. 5A including the bioprosthetic heart valve of FIG. 4 showing the concave landing zone positioned within an aorta.

FIG. 7 is a view of replacement valve system 20 positioned within an aorta A, which includes inflow annulus 64 and outflow annulus 66. As shown in FIG. 7, the tubular anchoring structure 24 of FIGS. 5A and/or 6A has expanded within the sinus cavities of aorta A, thereby forcing inflow rim 41 against inflow annulus 64 of aorta A to form a tight seal between replacement valve 22 and aorta A. More specifically, upon deployment inflow rim 41 assumes a substantially C-shaped in cross section concave landing zone 60 as can be seen in FIGS. 5B, 6B and 7. Distal inflow ring 49 abuts the distal side of the annulus while proximal inflow ring 51 abuts the proximal side of the native annulus. The concave landing zone 60 prevents and/or minimizes paravalvular leakage and migration of replacement valve 22 from the implantation site. Thus, with inflow ring 41 in contact with inflow annulus 64, the concave landing zone 60 acts as a gasket to seal the junction between replacement valve system 20 and aorta A. Typically, inflow ring 41 is covered with fabric to stimulate tissue ingrowth over time and secure the replacement heart valve in position. The fabric may comprise any suitable material including, but not limited to, woven polyester, polyester velour, polyethylene terepthalate, polytetrafluoroethylene (PTFE), or other biocompatible material. The valve assembly may be compressed in ice, loaded into a delivery system, and deployed into the aortic valve position. The self-expanding characteristic of the anchoring structure provides the radial strength required to hold the valve in position after implant.

Figure 9:
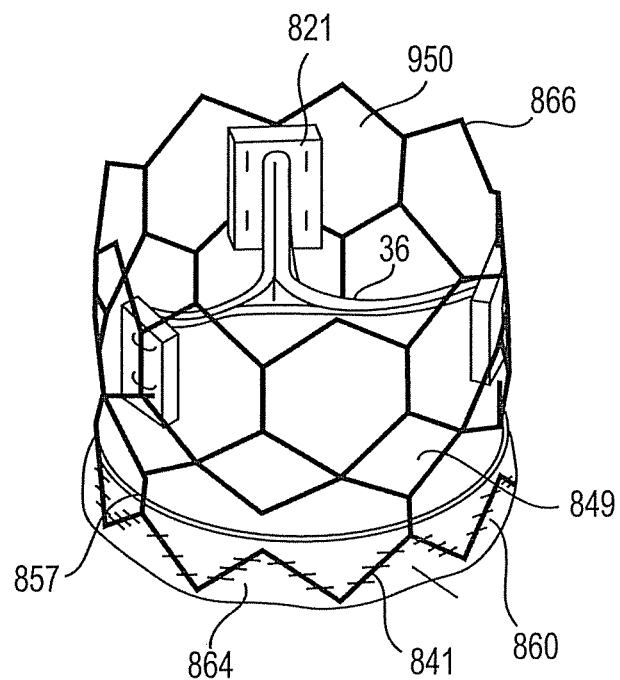
FIG. 9 depicts an alternative perspective view of the single rail flared or concave inflow rim of FIG. 8.

Turning now to FIGS. 8 and 9, yet another alternative embodiment of an anchoring structure with a concave landing zone in accordance with the principle of the invention is shown. A valve 822 supported by an anchoring structure 824 having a concave landing zone 860 is shown. Valve 822 includes optional sewing cuff 837. In this embodiment, anchoring structure 824 utilizes a diamond and hexagon shaped structure that facilitates collapsibility and dynamic compliance. Those skilled in the art however will appreciate that there are numerous designs for the anchoring structure that can be utilized. As can be seen from FIGS. 8 and 9, inflow ring 841 includes a single wire ring that is structured to flare out from the vertical support posts to anchor it firmly against the inflow valve sinus as hereinbefore disclosed.

Outflow ring 866 may optionally also be flared-out sections to anchor it against the outflow annuli of the valve sinuses. The flared outflow ring 866 of the anchoring structure 824 is adapted to support the tab regions 821 of the valve 822 while the single flared inflow ring 841 allows the anchoring structure 824 to be securely positioned in a sinus cavity of the vascular passageway. The flared inflow ring 841 of the anchoring structure 824 preferably comprises a single ring in the form of an undulating or zigzag pattern to which the valve's optional fabric ring or sewing cuff 837 can be sewn. The inflow ring 841 of the anchoring structure may be connected to the outflow ring 866 by vertical support posts that are positioned to coincide with the commissural posts of the native sinus region. However, it should be understood that the number of vertical support posts may be adapted to the number of native commissural posts present in the particular sinus region.

Those of ordinary skill in the art will appreciate that there are many different configurations that can be employed for the configuration of the single inflow rim 841. For example, each of the peaks and troughs may be substantially of the same vertical height. Alternatively, either of the peaks or troughs may be constructed to be shorter than the other depending on the anatomy of the particular patient and valve replacement involved. Those of ordinary skill in the art will appreciate, however, that both the single ring construction may be comprised of any number of vertical heights without deviating from the spirit of the invention.

It should be noted that the novel anchoring structure device and bioprosthetic valve system in accordance with the invention is designed to be fitted in the annulus without sutures of any kind. However, those of ordinary skill in the art will also appreciate that sutures may or may not be used to secure the bioprosthetic valve system in place in the annulus.

During manufacture, the anchoring structure is cut from a smaller tube and expanded and heat set to the final desired size. Depending on the design, the tips of the single inflow ring and the tips distal inflow ring and the proximal inflow ring in the double and triple constructions may be flared outwardly to form a concave region extending from the cylindrical body of the anchoring structure frame. Additional fingers, such as those shown in FIG. 5A, may be used in any of the constructions may be flared outwardly to assist in engaging the annulus and support the fabric covering.

Although the invention has been described with reference to preferred embodiments, workers skilled in the art will recognize that changes may be made in form and detail without departing from the spirit and scope of the invention.

What is claimed is:

1. A valve replacement system comprising:
a substantially tubular anchoring structure having an inflow end and an outflow end, the anchoring structure comprising:
an inflow rim at the inflow end comprising a substantially C-shaped in cross section concave landing zone, the inflow rim comprising a generally sinusoidal proximal inflow ring having a plurality of peaks extending towards the outflow end and a plurality of troughs extending towards the inflow end, a generally sinusoidal distal inflow ring having a plurality of peaks extending towards the outflow end and a plurality of troughs extending towards the inflow end, and a generally sinusoidal central inflow ring disposed between the proximal inflow ring and the distal inflow ring and having a having a plurality of peaks extending towards the outflow end and a plurality of troughs extending towards the inflow end, wherein the troughs of the distal inflow ring are operably connected to the peaks of the central inflow ring, and the troughs of the central inflow ring are operably connected to the peaks of the proximal inflow ring, the inflow rim being configured to expand and contact an annulus of a native valve upon deployment such that the proximal inflow ring abuts a proximal side of the annulus and the distal inflow ring abuts a distal side of the annulus;
an outflow rim at the outflow end; and
a plurality of longitudinal support posts connecting the inflow rim to the outflow rim, wherein each support post of the plurality of support posts comprises a substantially paddle-shaped blade having an axial slot therethrough and an elongated vertical member extending from the blade and having a width narrower than a width of the blade, wherein the elongated vertical member is connected to the inflow rim at a location of one of the troughs of the distal inflow ring; and
a bioprosthetic heart valve comprising a commissural tab operably coupled to one blade of one support post of the plurality of longitudinal support posts.

2. The valve replacement system of claim 1, wherein the anchoring structure further comprises a plurality of finger elements extending axially from the inflow rim.

3. The valve replacement system of claim 1, wherein the blade is connected to the outflow rim.

4. The valve replacement system of claim 1, wherein the plurality of longitudinal support posts comprises two support posts.

5. The valve replacement system of claim 1, wherein the plurality of longitudinal support posts comprises three support posts.

6. A valve replacement system comprising:
a substantially tubular anchoring structure having an inflow end and an outflow end, the anchoring structure comprising:
an inflow rim at the inflow end comprising a substantially C-shaped in cross section concave landing zone, the inflow rim comprising a generally sinusoidal proximal inflow ring having a plurality of peaks extending towards the outflow end and a plurality of troughs extending towards the inflow end and a generally sinusoidal distal inflow ring having a plurality of peaks extending towards the outflow end and a plurality of troughs extending towards the inflow end, wherein at least one of the plurality of peaks of the proximal inflow ring is operably connected with a trough of the plurality of troughs of the distal inflow ring, the inflow rim being configured to expand and contact an annulus of a native valve upon deployment such that the proximal inflow ring abuts a proximal side of the annulus and the distal inflow ring abuts a distal side of the annulus;
an outflow rim at the outflow end;
a plurality of longitudinal support posts connecting the inflow rim to the outflow rim, wherein each longitudinal support post of the plurality of longitudinal support posts comprises a substantially paddle-shaped blade having an axial slot therethrough and an elongated vertical member extending from the blade and having a width narrower than a width of the blade, wherein the elongated vertical member is connected to the inflow rim at a location of one of the troughs of the distal inflow ring; and a plurality of finger elements extending axially from a peak of the proximal inflow ring towards the inflow end and extending axially from a trough of the distal inflow ring towards the outflow end; and a bioprosthetic heart valve comprising a commissural tab operably coupled to one blade of one support post of the plurality of longitudinal support posts.

7. The valve replacement system of claim 6, wherein the outflow rim comprises a rail.

8. The valve replacement system of claim 6, wherein the blade is connected to the outflow rim.

9. The valve replacement system of claim 6, wherein the plurality of longitudinal support posts comprises two support posts.

10. The valve replacement system of claim 6, wherein the plurality of longitudinal support posts comprises three support posts.

* * * * *